US008703765B2

(12) United States Patent
Himmelsbach

(10) Patent No.: US 8,703,765 B2
(45) Date of Patent: Apr. 22, 2014

(54) CYCLIC INHIBITORS OF 11β-HYDROXYSTEROID DEHYDROGENASE 1

(75) Inventor: Frank Himmelsbach, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 161 days.

(21) Appl. No.: 13/375,238

(22) PCT Filed: Jun. 1, 2010

(86) PCT No.: PCT/EP2010/057581
§ 371 (c)(1),
(2), (4) Date: Jan. 4, 2012

(87) PCT Pub. No.: WO2010/139673
PCT Pub. Date: Dec. 9, 2010

(65) Prior Publication Data
US 2012/0172357 A1 Jul. 5, 2012

Related U.S. Application Data

(60) Provisional application No. 61/217,609, filed on Jun. 2, 2009.

(51) Int. Cl.
A61K 31/535 (2006.01)
(52) U.S. Cl.
USPC .............................. 514/228.8; 544/96; 544/97
(58) Field of Classification Search
CPC .............................................. C12Y 101/01146
USPC .................................... 514/228.8; 544/96, 97
See application file for complete search history.

(56) References Cited

U.S. PATENT DOCUMENTS

| 3,341,538 | A | 9/1967 | Block et al. |
| 3,378,587 | A | 4/1968 | Reinhardt |
| 3,919,047 | A | 11/1975 | Vidic et al. |
| 4,043,927 | A | 8/1977 | Duling et al. |
| 4,108,857 | A | 8/1978 | Albertson |
| 4,268,673 | A | 5/1981 | Akkerman et al. |
| 6,145,103 | A | 11/2000 | Typaldos et al. |
| 7,897,773 | B2 | 3/2011 | Aletru et al. |
| 2006/0089349 | A1 | 4/2006 | Gundertofte et al. |
| 2006/0194780 | A1 | 8/2006 | Nargund et al. |
| 2009/0170894 | A1 | 7/2009 | Aletru et al. |
| 2010/0256363 | A1 | 10/2010 | Xu |
| 2011/0015157 | A1 | 1/2011 | Claremon et al. |
| 2011/0028445 | A1 | 2/2011 | Eckhardt et al. |
| 2011/0112062 | A1 | 5/2011 | Claremon et al. |
| 2011/0136800 | A1 | 6/2011 | Eckhardt et al. |
| 2011/0190262 | A1 | 8/2011 | Himmelsbach et al. |
| 2011/0269736 | A1 | 11/2011 | Eckhardt et al. |
| 2011/0269791 | A1 | 11/2011 | Peters et al. |
| 2011/0275595 | A1 | 11/2011 | Eckhardt et al. |
| 2012/0115853 | A1 | 5/2012 | Eckhardt et al. |
| 2012/0172357 | A1 | 7/2012 | Himmelsbach |

FOREIGN PATENT DOCUMENTS

| EP | 1864971 A1 | 12/2007 |
| EP | 1935420 A1 | 6/2008 |
| FR | 2796940 A1 | 2/2001 |
| GB | 1077711 A | 8/1967 |
| JP | 2007140188 A | 6/2007 |
| WO | 9852940 A1 | 11/1998 |
| WO | 0155063 A1 | 8/2001 |
| WO | 2004089896 A1 | 10/2004 |
| WO | 2005108361 A1 | 11/2005 |
| WO | 2006024628 A1 | 3/2006 |
| WO | 2006040329 A1 | 4/2006 |
| WO | 2006044174 A2 | 4/2006 |
| WO | 2007051810 A2 | 5/2007 |
| WO | 2007076055 A2 | 7/2007 |
| WO | 2008000951 A2 | 1/2008 |
| WO | 2009017664 A1 | 2/2009 |

(Continued)

OTHER PUBLICATIONS

De Luis et al., Control of Metabolic Syndrome with Metformin in Obese Type 2 Diabetes Mellitus Patients, Diabetes Research and Clinical Practice, 2000, vol. 50, Suppl. 1, pp. S51-552.
Gutkowska, et al, Acta Poloniae Pharmaceutica, 1982, 39, p. 61-64.
Olesen, Preben H.; the Use of Bioisosteric Groups in Lead Optimization; Current Opinion in Drug Discovery & Development (2001) vol. 4, No. 4 pp. 471-478.
Patani, George A. et al., "Bioisosterism: A Rational Approach in Drug Design" Chem. Rev. (1996) vol. 96, pp. 3147-3176.
Thornber, C.W.; Isosterism and Molecular Modification in Drug Design; Chem. Soc, Rev (1979) vol. 8 pp. 563-580.

(Continued)

Primary Examiner — Jason Sims
Assistant Examiner — Ibrahim D Bori
(74) Attorney, Agent, or Firm — Michael P. Morris; David L. Kershner

(57) ABSTRACT

This invention relates to novel compounds of the Formula (I), dependent compounds of Formula (II), (II-A), (II-B), (II-C), (II-D), (II-E), (II-F), (II-G), (II-H), (III), (III-A), (III-B), (III-C), (IV), (IV-A), (IV-B), pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to cortisol in a cell.

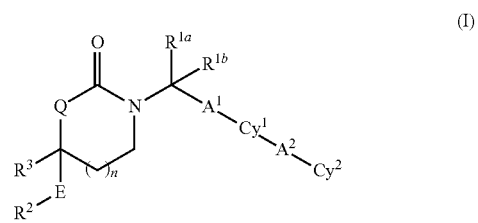

(I)

16 Claims, No Drawings

(56) References Cited

FOREIGN PATENT DOCUMENTS

| | | |
|---|---|---|
| WO | 2009017671 A1 | 2/2009 |
| WO | 2009061498 A1 | 5/2009 |
| WO | 2009063061 A2 | 5/2009 |
| WO | 2009100872 A1 | 8/2009 |
| WO | 2009102428 A2 | 8/2009 |
| WO | 2009117109 A1 | 9/2009 |
| WO | 2009138386 A2 | 11/2009 |
| WO | 2010010157 A2 | 1/2010 |
| WO | 2010010174 A1 | 1/2010 |
| WO | 2010023161 A1 | 3/2010 |
| WO | 2010046445 A2 | 4/2010 |
| WO | 2010139673 A1 | 12/2010 |
| WO | 2011057054 A1 | 5/2011 |
| WO | 2012061708 A1 | 5/2012 |

OTHER PUBLICATIONS

Abstract in English for JP2007140188 publication date 2007.
Caplus-133:4656—Anantanarayan, A. et. al., "Preparation of heteroarylpyrazoles as P38 kinase inhibitors". 2000.
Caplus-147:134403, Hembrough, T.A., et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
ChemAbstract—Accession No. 958599-31-0, Chemical Abstracts Service, Columbus, Ohio, Source: Emory MLSC database, Dec. 2007.
ChemAbstract—Accession No. 958625-83-7, Chemical Abstracts Service, Columbus, Ohio, Source: Emory MLSC database, Dec. 2007.
ChemAbstract—Accession No. 958629-14-6, Chemical Abstracts Service, Columbus, Ohio, Source: Emory MLSC database, Dec. 2007.
ChemAbstract—Accession No. 958629-22-6, Chemical Abstracts Service, Columbus, Ohio, Source: Emory MLSC database, Dec. 2007.
ChemAbstract—Accession No. 958629-39-5, Chemical Abstracts Service, Columbus, Ohio, Source: Emory MLSC database, Dec. 2007.
ChemAbstract—Accession No. 958696-32-7, Chemical Abstracts Service, Columbus, Ohio, Source: Emory MLSC database, Dec. 2007.
ChemAbstract-Accession No. 958696-39-4, Chemical Abstracts Service, Columbus, Ohio, Source: Emory MLSC database, Dec. 2007.
ChemAbstract—Accession No. 958700-63-5, Chemical Abstracts Service, Columbus, Ohio, Source: Emory MLSC database, Dec. 2007.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report and Written Opinion for PCT/EP2010/057581 mailed Aug. 25, 2010.
WO09017664 Published Feb. 5, 2009. Applicant: Vitae Pharmaceuticals, Inc. Inventor: D. A. Claremon et al. This foreign patent is over 25KB and will not upload using EFS. Also published as US Publication US2011015157 and US201025636.

CYCLIC INHIBITORS OF 11β-HYDROXYSTEROID DEHYDROGENASE 1

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula (I) or pharmaceutically acceptable salts thereof, are effective inhibitors of 11β-HSD1.

The present invention is directed to compounds represented by the Structural Formula (I):

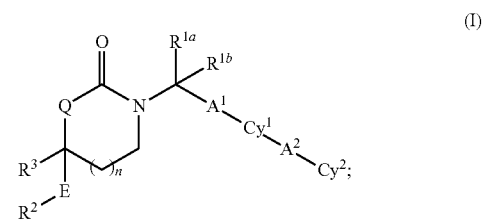

or a pharmaceutically acceptable salt, enantiomer or diastereomer thereof.

$R^{1a}$ is $(C_3-C_7)$cycloalkyl optionally substituted with up to four groups independently selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino $(C_1-C_6)$alkyl, hydroxy$(C_1-C_6)$alkyl, $(C_1-C_6)$alkoxy$(C_1-C_6)$alkyl, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl, heteroaryl, arylamino and heteroarylamino.

$R^{1b}$ is hydrogen, $(C_1-C_6)$alkyl, $(C_2-C_6)$alkenyl, $(C_2-C_6)$alkynyl or $(C_1-C_3)$alkoxy$(C_1-C_3)$alkyl, and the $(C_1-C_6)$alkyl, $(C_2-C_6)$alkenyl, $(C_2-C_6)$alkynyl and $(C_1-C_3)$alkoxy$(C_1-C_3)$alkyl, and the group represented by $R^{1b}$ is optionally substituted with up to four groups independently selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl, heteroaryl, arylamino and heteroarylamino.

$A^1$ is (a) a bond, (b) $(C_1-C_2)$alkylene or $CH_2O$ with the oxygen being attached to $Cy^1$ or $C(=O)$, or (c) $(C_2-C_4)$alkynyl.

$Cy^1$ is aryl, heteroaryl, monocyclic cycloalkyl or monocyclic heterocyclyl and is optionally substituted with 1 to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —$R^9$, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1-NHC(=O)R^6$, —$NHS(=O)_2R^6$, —$V^1-NHS(=O)_2R^6$, —$V^1-C(=O)R^6$, heteroaryl, aryl, heterocyclyl, oxo, —$V^1-NH_2$, —$V^1-NHR^6$, —$V^1-N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1-C_6)$alkyl, —$V^1-C(=O)NH_2$, —$V^1-C(=O)NHR^6$, —$V^1-C(=O)N(R^6)_2$, —$V^1-C(=O)NHR^7$, —$V^1-C(=O)NR^6R^7$ and —$V^1-C(=O)N(R^7)_2$.

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo.

$Cy^2$ is (a) hydrogen or (b) aryl, heteroaryl, cycloalkyl or heterocyclyl and is optionally substituted with 1 to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —$R^9$, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1-NHC(=O)R^6$, —$NHS(=O)_2R^6$, —$V^1-NHS(=O)_2R^6$, —$V^1-C(=O)R^6$, heteroaryl, aryl, heterocyclyl, oxo, —$V^1-NH_2$, —$V^1-NHR^6$, —$V^1-N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1-C_6)$alkyl, —$V^1-C(=O)NH_2$, —$V^1-C(=O)NHR^6$, —$V^1-C(=O)N(R^6)_2$, —$V^1-C(=O)NHR^7$, —$V^1-C(=O)NR^6R^7$, and —$V^1-C(=O)N(R^7)_2$.

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo.

$R^2$ is $(C_1-C_6)$alkyl, aryl, heteroaryl, cycloalkyl or heterocyclyl and is optionally substituted with up to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —$R^9$, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1-NHC(=O)R^6$, —$NHS(=O)_2R^6$, —$V^1-NHS(=O)_2R^6$, —$V^1-C(=O)R^6$, heteroaryl, aryl, heterocyclyl, oxo, —$V^1-NH_2$, —$V^1-NHR^6$, —$V^1-N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R)_2$, cyano$(C_1-C_6)$alkyl, —$V^1-C(=O)NH_2$, —$V^1-C(=O)NHR^6$, —$V^1-C(=O)N(R^6)_2$, —$V^1-C(=O)NHR^7$, —$V^1-C(=O)NR^6R^7$ and —$V^1-C(=O)N(R^7)_2$.

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O-$, $(R^4)_2N-$, $R^4O_2C-$, $R^4C(=O)O-$, $R^4S-$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS (=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, spirocycloalkyl; heterocyclyl (which in turn is optionally substituted with alkyl, haloalkyl, halogen or oxo), heteroaryl (which in turn is optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), aryl-amino (which in turn may be optionally substituted with alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido) and heteroarylamino (which in turn is optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo).

n is 0, 1 or 2.

Q is O, CH$_2$ or NR$^5$.

each R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino (C$_1$-C$_6$)alkyl, di(C$_1$-C$_6$)alkylamino(C$_1$-C$_6$)alkyl, hydroxy (C$_1$-C$_6$)alkyl and (C$_1$-C$_6$)alkoxy(C$_1$-C$_6$)alkyl.

each R$^5$ is independently H, (C$_1$-C$_6$)alkyl, halo(C$_1$-C$_6$)alkyl or hydroxy(C$_1$-C$_6$)alkyl.

each R$^6$ is independently (C$_1$-C$_6$)alkyl, (C$_2$-C$_6$)alkenyl, (C$_2$-C$_6$)alkynyl or (C$_1$-C$_6$)alkoxy.

V$^1$ is (C$_1$-C$_6$)alkylene, (C$_1$-C$_6$)alkenylene, (C$_1$-C$_6$)alkynylene or (C$_1$-C$_6$)alkyleneoxy.

each R$^7$ is independently (C$_3$-C$_6$)cycloalkyl or (C$_3$-C$_6$)cycloalkoxy.

R$^8$ is heterocyclyl.

R$^9$ is (C$_4$-C$_7$)cycloalkylalkyl, (C$_4$-C$_7$)cycloalkylalkoxy, (C$_3$-C$_6$)cycloalkyl(C$_2$-C$_4$)alkynyl, halo(C$_1$-C$_6$)alkyl, halo (C$_2$-C$_6$)alkenyl, halo(C$_3$-C$_6$)cycloalkyl, halo(C$_4$-C$_7$)cycloalkylalkyl, halo(C$_1$-C$_6$)alkoxy, halo(C$_3$-C$_6$)cycloalkoxy, halo(C$_4$-C$_7$)cycloalkylalkoxy, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxy(C$_1$-C$_6$)alkyl or halo(C$_1$-C$_6$)alkoxy(C$_1$-C$_6$)alkyl.

Another embodiment of the invention is a pharmaceutical composition comprising i) a pharmaceutically acceptable carrier or diluent, and ii) a compound of Formulas (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of an 11β-HSD1 inhibitor disclosed herein.

Another embodiment of the invention is the use of a compound of an 11β-HSD1 inhibitor disclosed herein for the manufacture of a medicament for inhibiting 11β-HSD1 activity in a mammal in need of such treatment.

Another embodiment of the invention is the use of an 11β-HSD1 inhibitor disclosed herein for the manufacture of a medicament for treating a subject with a disease associated with the activity or expression of 11β-HSD1.

Another embodiment of the invention is an 11β-HSD1 disclosed herein for use in inhibiting 11β-HSD1 activity in a mammal in need of such treatment.

Another embodiment of the invention is an 11β-HSD1 inhibitor disclosed herein for use in for treating a subject with a disease associated with the activity or expression of 11β-HSD1.

DETAILED DESCRIPTION OF THE INVENTION

The present invention is directed to compounds represented by the Structural Formula (I) or a pharmaceutically acceptable salt, enantiomer or diastereomer thereof. Values and particular values for the variables in Structural Formula I or an enantiomer, a diastereomer, or a pharmaceutically acceptable salt thereof are provided in the following paragraphs. It is understood that the invention encompasses all combinations of the substituent variables (i.e., Cy$^1$, R2, R3, etc.) defined herein. For Structural Formula (I):

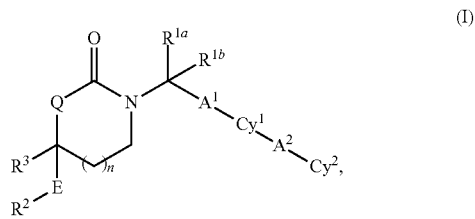

or a pharmaceutically acceptable salt, enantiomer or diastereomer thereof:

R$^{1a}$ is (C$_3$-C$_7$)cycloalkyl optionally substituted with up to four groups independently selected from —H, fluorine, cyano, oxo, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino (C$_1$-C$_6$)alkyl, hydroxy(C$_1$-C$_6$)alkyl, (C$_1$-C$_6$)alkoxy(C$_1$-C$_6$)alkyl, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclyl, heteroaryl, arylamino and heteroarylamino.

In one particular embodiment, R$^{1a}$ is optionally substituted (C$_3$-C$_5$)cycloalkyl.

In a more particular embodiment, R$^{1a}$ is optionally substituted cyclopropyl.

In another particular embodiment, R$^{1a}$ is (C$_3$-C$_7$)cycloalkyl optionally substituted with up to four groups independently selected from fluorine, cyano, oxo, (C$_1$-C$_6$)alkyl, halo(C$_1$-C$_6$)alkyl, amino(C$_1$-C$_6$)alkyl, (C$_1$-C$_6$)alkylamino ($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In a more particular embodiment, $R^{1a}$ is ($C_3$-$C_5$)cycloalkyl optionally substituted with up to four groups independently selected from fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In an even more particular embodiment, $R^{1a}$ is cyclopropyl optionally substituted with up to four groups independently selected from fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In another particular embodiment, $R^{1a}$ is unsubstituted ($C_3$-$C_7$)cycloalkyl.

In a more particular embodiment, $R^{1a}$ is unsubstituted ($C_3$-$C_5$)cycloalkyl.

In an even more particular embodiment, $R^{1a}$ is unsubstituted cyclopropyl.

$R^{1b}$ is hydrogen, ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl, and the ($C_1$-$C_6$)alkyl, ($C_2$-$C_6$)alkenyl, ($C_2$-$C_6$)alkynyl and ($C_1$-$C_3$)alkoxy($C_1$-$C_3$)alkyl, and the group represented by $R^{1b}$ is optionally substituted with up to four groups independently selected from —H, fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino.

In one particular embodiment, $R^{1b}$ is hydrogen or optionally substituted ($C_1$-$C_6$)alkyl.

In a more particular embodiment, $R^{1b}$ is hydrogen or optionally substituted methyl.

In another particular embodiment, $R^{1b}$ is hydrogen or ($C_1$-$C_6$)alkyl optionally substituted with up to four groups independently selected from fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In a more particular embodiment, $R^{1b}$ is hydrogen or methyl optionally substituted with up to three groups independently selected from fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In another particular embodiment, $R^{1b}$ is ($C_1$-$C_6$)alkyl optionally substituted with up to four groups independently selected from fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In a more particular embodiment, $R^{1b}$ is methyl optionally substituted with up to three groups independently selected from fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl and $R^4O$—.

In another particular embodiment, $R^{1b}$ is unsubstituted ($C_1$-$C_6$)alkyl.

In a more particular embodiment, $R^{1b}$ is unsubstituted methyl.

In an even more particular embodiment, $R^{1b}$ is H.

$A^1$ is (a) a bond, (b) ($C_1$-$C_2$)alkylene or $CH_2O$ with the oxygen being attached to $Cy^1$ or $C(=O)$, or (c) ($C_2$-$C_4$)alkynyl.

In one particular embodiment, $A^1$ is a bond.

In another particular embodiment, $A^1$ is a ($C_1$-$C_2$)alkylene.

In another particular embodiment, $A^1$ is a ($C_2$-$C_4$)alkynyl.

In a more particular embodiment, $A^1$ is a ethynyl.

$Cy^1$ is aryl, heteroaryl, monocyclic cycloalkyl or monocyclic heterocyclyl and is optionally substituted with 1 to 4 groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, —$R^9$, ($C_1$-$C_6$)alkylthio, ($C_3$-$C_6$)cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano($C_1$-$C_6$)alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$.

In one particular embodiment, $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group.

In a more particular embodiment, $Cy^1$ is an optionally substituted cyclohexyl, phenyl, pyridyl, pyrimidinyl, thiazolyl, triazolyl, piperidinyl, pyrrolidinyl or benzothiazolyl.

In an even more particular embodiment, $Cy^1$ is optionally substituted phenyl.

In another particular embodiment, the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl.

In another particular embodiment, the group represented by $Cy^1$ is optionally substituted with fluoro, chloro, bromo, cyano, $CONH_2$, $CONHMe$, $CONMe_2$, methyl, ethyl, cyclopropyl, $CHF_2$, $CHF_2CH_2$, $OCHF_2$, $OCHF_2CH_2$ or $CF_3$.

In another particular embodiment, the group represented by $Cy^1$ is optionally substituted with fluoro, chloro, bromo, methyl, ethyl, cyclopropyl, $OCHF_2$, or $CF_3$.

In another particular embodiment, $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl.

In a more particular embodiment, $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and the group represented by $Cy^1$ is optionally substituted with fluoro, chloro, bromo, methyl, ethyl, cyclopropyl, $OCHF_2$ or $CF_3$.

In another particular embodiment, $Cy^1$ is phenyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl.

In another particular embodiment, $Cy^1$ is phenyl optionally substituted with fluoro, chloro, bromo, methyl, ethyl, cyclopropyl, $OCHF_2$, or $CF_3$.

In another particular embodiment, $Cy^1$ is phenyl optionally substituted with fluoro, chloro, or methyl.

In an even more particular embodiment, $Cy^1$ is phenyl.

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo.

In one particular embodiment, $A^2$ is a bond.

In another particular embodiment, $A^2$ is $(C_1-C_3)$alkylene or $(C_1-C_2)$alkyleneoxy, each of which is optionally substituted with 1 to 4 groups independently selected from methyl, ethyl, trifluoromethyl or oxo.

In a more particular embodiment, $A^2$ is $(C_1-C_3)$alkylene optionally substituted with 1 to 4 groups independently selected from methyl, ethyl, trifluoromethyl or oxo.

In an even more particular embodiment, $A^2$ is unsubstituted $(C_1-C_3)$alkylene.

$Cy^2$ is (a) hydrogen or (b) aryl, heteroaryl, cycloalkyl or heterocyclyl and is optionally substituted with 1 to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —$R^9$, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)R^6$, —$V^1$—$NHS(=O)_2R^6$, —$V^1$—$C(=O)$ $R^6$, heteroaryl, aryl, heterocyclyl, oxo, —$V^1$—NH2, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1-C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$, and —$V^1$—$C(=O)N(R^7)_2$.

In one particular embodiment, $Cy^2$ is an optionally substituted aryl, heteroaryl, cycloalkyl or heterocyclyl group.

In a more particular embodiment, $Cy^2$ is an optionally substituted aryl, heteroaryl, cycloalkyl or heterocyclyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, cyano, carbamoyl, methylcarbamoyl, dimethylcarbamoyl, (2-methoxyethyl)aminocarbonyl, acetylaminomethyl, methylsulfonyl, cyclopropylaminocarbonyl, methylsulfonylamino, N-methyl-methylsulfonylamino, methylaminosulfonyl, isopropylaminosulfonyl, dimethylaminosulfonyl, pyrrolidine-1-sulfonyl, methylsulfonylaminomethyldifluoromethyl, trifluoromethyl, 2-fluoroethyl, acetyl, 1-hydroxyethyl, 2-hydroxyethyl and 2-hydroxy-2-propyl.

In another more particular embodiment, $Cy^2$ is an optionally substituted aryl, heteroaryl, cycloalkyl or heterocyclyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, or oxodihydrotriazolopyridinyl group.

In a more particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl.

In an even more particular embodiment, $Cy^2$ is an optionally substituted phenyl, pyridyl, pyridazinyl, pyrimidinyl or oxodihydropyridyl group.

In an even more particular embodiment, $Cy^2$ is an optionally substituted oxodihydropyridyl group.

In another particular embodiment, the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, cyano, carbamoyl, methylcarbamoyl, dimethylcarbamoyl, (2-methoxyethyl)aminocarbonyl, acetylaminomethyl, methylsulfonyl, acetylaminomethyl, methylsulfonyl, methylsulfonylamino, N-methyl-methylsulfonylamino, methylaminosulfonyl, isopropylaminosulfonyl, dimethylaminosulfonyl, pyrrolidine-1-sulfonyl, methylsulfonylaminomethyldifluoromethyl, trifluoromethyl, 2-fluoroethyl, acetyl, 1-hydroxyethyl, 2-hydroxyethyl and 2-hydroxy-2-propyl.

In another particular embodiment, the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl.

In another particular embodiment, the group represented by $Cy^2$ is optionally substituted with fluoro, chloro, bromo, cyano, $CONH_2$, CONHMe, $CONMe_2$, methyl, ethyl, cyclopropyl, $CHF_2$, $CHF_2CH_2$ or $CF_3$.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, or oxodihydrotriazolopyridinyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, cyano, carbamoyl, methylcarbamoyl, dimethylcarbamoyl, (2-methoxyethyl)aminocarbonyl, acetylaminomethyl, methylsulfonyl, acetylaminomethyl, methylsulfonyl, methylsulfonylamino, N-methyl-methylsulfonylamino, methylaminosulfonyl, isopropylaminosulfonyl, dimethylaminosulfonyl, pyrrolidine-1-sulfonyl, methylsulfonylaminomethyldifluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, or oxodihydrotriazolopyridinyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, cyano, carbamoyl, methylcarbamoyl, dimethylcarbamoyl, (2-methoxyethyl)aminocarbonyl, acetylaminomethyl, methylsulfonyl, acetylaminomethyl, methylsulfonyl, methylsulfonylamino, N-methyl-methylsulfonylamino, methylaminosulfonyl, isopropylaminosulfonyl, dimethylaminosulfonyl, pyrrolidine-1-sulfonyl, methylsulfonyl-aminomethyldifluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methyl-carbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl or oxodihydropyridyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, cyano, carbamoyl, methylcarbamoyl, dimethylcarbamoyl, (2-methoxyethyl)aminocarbonyl, acetylaminomethyl, methylsulfonyl, acetylaminomethyl, methylsulfonyl, methylsulfonylamino, N-methyl-methylsulfonylamino, methylaminosulfonyl, isopropylaminosulfonyl, dimethylaminosulfonyl, pyrrolidine-1-sulfonyl, methylsulfonylaminomethyldifluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl or oxodihydropyridyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is an optionally substituted phenyl, pyridyl, pyridazinyl, pyrimidinyl or oxodihydropyridyl group, and the group represented by $Cy^2$ is optionally substituted with fluoro, chloro, bromo, cyano, $CONH_2$, CONHMe, $CONMe_2$, methyl, ethyl, cyclopropyl, $CHF_2$, $CHF_2CH_2$ or $CF_3$.

In another particular embodiment, $Cy^2$ is an optionally substituted pyridyl, pyridazinyl or pyrimidinyl group, and the group represented by $Cy^2$ is optionally substituted with cyano, $CONH_2$, CONHMe, $CONMe_2$, cyclopropylaminocarbonyl, N-methyl-methylsulfonylamino, methyl, ethyl, isopropyl, cyclopropyl, $CHF_2$ or $CF_3$.

In another particular embodiment, $Cy^2$ is an optionally substituted pyridyl, pyridazinyl or pyrimidinyl group, and the group represented by $Cy^2$ is optionally substituted with cyano, $CONH_2$, CONHMe, $CONMe_2$, methyl, ethyl, isopropyl or cyclopropyl.

In another particular embodiment, $Cy^2$ is an optionally substituted pyridazinyl or pyrimidinyl group, and the group represented by $Cy^2$ is optionally substituted with methyl, ethyl, isopropyl or cyclopropyl.

In another particular embodiment, $Cy^2$ is oxodihydropyridyl optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methyl-carbamoyl, dimethylcarbamoyl, methylsulfonyl, methylsulfonylamino, N-methyl-methylsulfonylamino, difluoromethyl, trifluoromethyl, 2-fluoroethyl, acetyl, 1-hydroxyethyl, 2-hydroxyethyl and 2-hydroxy-2-propyl.

In another particular embodiment, $Cy^2$ is oxodihydropyridyl optionally substituted with 1 or 2 groups independently selected from methyl, ethyl, propyl, isopropyl, cyclopropyl, difluoromethyl or 2-fluoroethyl.

In another particular embodiment, $Cy^2$ is oxodihydropyridyl optionally substituted with fluoro, chloro, bromo, cyano, $CONH_2$, CONHMe, $CONMe_2$, methyl, ethyl, cyclopropyl, $CHF_2$, $CHF_2CH_2$ or $CF_3$.

In another particular embodiment, $Cy^2$ is oxodihydropyridyl optionally substituted at the ring nitrogen with methyl, ethyl, propyl, cyclopropyl, difluoromethyl, 2-fluoroethyl or 2,2,2-trifluoroethyl.

In another particular embodiment, $Cy^2$ is oxodihydropyridyl optionally substituted at the ring nitrogen with methyl, ethyl, propyl or cyclopropyl.

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo.

In one particular embodiment, E is a bond or unsubstituted $(C_1-C_3)$alkylene.

In a more particular embodiment, E is a bond.

$R^2$ is $(C_1-C_6)$alkyl, aryl, heteroaryl, cycloalkyl or heterocyclyl and is optionally substituted with up to 4 groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —$R^9$, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R)_2$, cyano$(C_1-C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$.

In one particular embodiment, $R^2$ is an optionally substituted $(C_1-C_6)$alkyl, aryl, heteroaryl or cycloalkyl group.

In a more particular embodiment, $R^2$ is an optionally substituted phenyl, fluorophenyl, isopropyl, cyclopropyl, t-butyl, cyclopropylmethyl or trifluoroethyl group.

In another particular embodiment, $R^2$ is an optionally substituted $(C_1-C_6)$alkyl, aryl, heteroaryl or cycloalkyl group; each optionally substituted with up to four groups independently selected from halogen, —CN, —$NO_2$, —$NH_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, and $(C_3-C_6)$cycloalkythio.

In a more particular embodiment, $R^2$ is a phenyl, fluorophenyl, isopropyl, cyclopropyl, t-butyl, cyclopropylmethyl or trifluoroethyl, each optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen and cyano.

In yet a more particular embodiment, $R^2$ is phenyl optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen and cyano.

In yet another more particular embodiment, $R^2$ is phenyl or fluorophenyl.

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4C(=O)O$—, $R^4S$—, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn is optionally substituted with alkyl, haloalkyl, halogen or oxo), heteroaryl (which in turn is optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), aryl-amino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn is optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

In one particular embodiment, $R^3$ is $(C_3-C_6)$alkenyl, hydroxy$(C_2-C_5)$alkyl, cyano$(C_2-C_5)$alkyl, dihydroxy$(C_3-C_5)$alkyl, ω-$H_2NCO(C_1-C_5)$alkyl, $(C_1-C_2)$alkoxy$(C_1-C_4)$alkyl, $H_2NSO_2O(C_2-C_5)$alkyl, $H_2NSO_2NH(C_2-C_5)$alkyl, oxo$(C_2-C_5)$alkyl, MeC$(=O)$NH$(C_2-C_5)$alkyl, $MeSO_2NH(C_2-C_5)$alkyl, or $MeSO_2NH(C_2-C_5)$alkyl In another particular embodiment, $R^3$ is methyl, ethyl, propyl, butyl, vinyl, allyl or ethoxyethyl each optionally substituted with up to two groups independently selected from methyl, HO—, MeO—, $H_2N$—, MeC$(=O)$NH—, MeS$(=O)_2$NH—, $H_2NC(=O)$—, MeNHC$(=O)$—, $HO_2C$—, $(HO)_2P(=O)O$—, $H_2NS(=O)_2O$—, $H_2NS(=O)_2NH$—, MeNHC$(=O)$NH—, MeNHC$(=O)O$—, oxo, cyano, $HO_2C$—, $HOCH_2CH_2NH$—, 4-morpholino, $HOCH_2C(=O)$ NH—, H$_2$NCH$_2$C(=O)NH—, EtNHC(=O)NH, MeOC(=O)NH—, MeNHC(=NC=N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe.

In a more particular embodiment, R$^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, MeNHC(=O)NH—, oxo, cyano, HOCH$_2$C(=O)NH—, EtNHC(=O)NH, MeS—, MeSO$_2$—MeSO$_2$N(Me)-, 2-oxo-1-pyrrolidinyl, H$_2$NCONH—, H$_2$NCO$_2$—, HOCH$_2$CH$_2$O—, MeNH—, Me$_2$N— and MeCONMe.

In yet a more particular embodiment, R$^3$ is 2-methylallyl, MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

In an even more particular embodiment, R$^3$ is 2-methylallyl, 2-hydroxy-2-methylpropyl or 2-cyano-2-methylpropyl.

n is 0, 1 or 2.

In a particular embodiment, n is 1.

Q is O, CH$_2$ or NR$^5$.

In a particular embodiment, Q is O.

each R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl.

each R$^5$ is independently H, (C$_1$-C$_6$)alkyl, halo(C$_1$-C$_6$)alkyl or hydroxy(C$_1$-C$_6$)alkyl.

each R$^6$ is independently (C$_1$-C$_6$)alkyl, (C$_2$-C$_6$)alkenyl, (C$_2$-C$_6$)alkynyl or (C$_1$-C$_6$)alkoxy.

V$^1$ is (C$_1$-C$_6$)alkylene, (C$_1$-C$_6$)alkenylene, (C$_1$-C$_6$)alkynylene or (C$_1$-C$_6$)alkyleneoxy.

each R$^7$ is independently (C$_3$-C$_6$)cycloalkyl or (C$_3$-C$_6$)cycloalkoxy.

R$^8$ is heterocyclyl.

R$^9$ is (C$_4$-C$_7$)cycloalkylalkyl, (C$_4$-C$_7$)cycloalkylalkoxy, (C$_3$-C$_6$)cycloalkyl(C$_2$-C$_4$)alkynyl, halo(C$_1$-C$_6$)alkyl, halo(C$_2$-C$_6$)alkenyl, halo(C$_3$-C$_6$)cycloalkyl, halo(C$_4$-C$_7$)cycloalkylalkyl, halo(C$_1$-C$_6$)alkoxy, halo(C$_3$-C$_6$)cycloalkoxy, halo(C$_4$-C$_7$)cycloalkylalkoxy, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxy(C$_1$-C$_6$)alkyl or halo(C$_1$-C$_6$)alkoxy(C$_1$-C$_6$)alkyl.

In a 1$^{st}$ specific embodiment, the compound of the present invention is represented by Structural Formula (II):

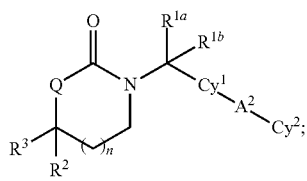

(II)

or a pharmaceutically acceptable salt, enantiomer or diastereomer thereof.

R$^{1a}$ is optionally substituted (C$_3$-C$_5$)cycloalkyl, R$^{1b}$ is hydrogen or optionally substituted (C$_1$-C$_6$)alkyl, and Cy$^2$ is an optionally substituted aryl, heteroaryl, cycloalkyl or heterocyclyl group, and values and particular values for the remainder of the variables in Structural Formula (II) are as described above for Structural Formula (I).

In a more specific embodiment, for compounds of Structural Formula (II), Cy$^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and values and particular values for the remainder of the variables in Structural Formula (II) are as described above for Structural Formula (I).

In another more specific embodiment, for compounds of Structural Formula (II), R$^{1a}$ is optionally substituted (C$_3$-C$_5$)cycloalkyl, R$^{1b}$ is hydrogen or optionally substituted (C$_1$-C$_6$)alkyl, Cy$^2$ is an optionally substituted aryl, heteroaryl, cycloalkyl or heterocyclyl group, and Cy$^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and values and particular values for the remainder of the variables in Structural Formula (II) are as described above for Structural Formula (I).

In a 2$^{nd}$ specific embodiment, the compound of the present invention is represented by Structural Formula (II-A):

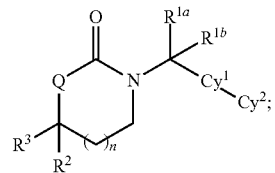

(II-A)

or a pharmaceutically acceptable salt, enantiomer or diastereomer thereof.

The values and specific values for the variables in Structural Formula (II-A) are as described above for Structural Formula (II).

In a more specific embodiment, for compounds of Structural Formula (II-A),

R$^{1a}$ is optionally substituted cyclopropyl, and values and specific values for the remainder of the variables in Structural Formula (II-A) are as described above for Structural Formula (II).

In a 3$^{rd}$ specific embodiment, the compound of the present invention is represented by Structural Formula (II-B):

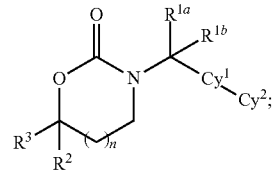

(II-B)

or a pharmaceutically acceptable salt, enantiomer or diastereomer thereof.

The values and specific values for the variables in Structural Formula (II-B) are as described above for Structural Formula (II-A).

In a 4th specific embodiment, the compound of the present invention is represented by Structural Formula (II-C):

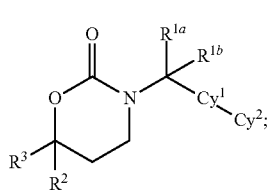

(II-C)

or a pharmaceutically acceptable salt, enantiomer or diastereomer thereof.

The values and specific values for the variables in Structural Formula (II-C) are as described above for Structural Formula (II-A).

In a more specific embodiment, for compounds of Structural Formula (II-C), $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, or oxodihydrotriazolopyridinyl group, and values and specific values for the remainder of the variables in Structural Formula (II-C) are as described above for Structural Formula (II-A).

In another more specific embodiment, for compounds of Structural Formula (II-C), $R^{1b}$ is hydrogen or optionally substituted methyl, and values and specific values for the remainder of the variables in Structural Formula (II-C) are as described above for Structural Formula (II-B).

In yet another more specific embodiment, for compounds of Structural Formula (II-C), $R^{1b}$ is hydrogen or optionally substituted methyl, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, or oxodihydrotriazolopyridinyl group, and values and specific values for the remainder of the variables in Structural Formula (II-C) are as described above for Structural Formula (II-B).

In yet another more specific embodiment, for compounds of Structural Formula (II-C), $Cy^1$ is an optionally substituted cyclohexyl, phenyl, pyridyl, pyrimidinyl, thiazolyl, triazolyl, piperidinyl, pyrrolidinyl or benzothiazolyl, and values and specific values for the remainder of the variables in Structural Formula (II-C) are as described above for Structural Formula (II-B).

In yet another more specific embodiment, for compounds of Structural Formula (II-C), $R^{1b}$ is hydrogen or optionally substituted methyl, $Cy^1$ is an optionally substituted cyclohexyl, phenyl, pyridyl, pyrimidinyl, thiazolyl, triazolyl, piperidinyl, pyrrolidinyl or benzothiazolyl, and values and specific values for the remainder of the variables in Structural Formula (II-C) are as described above for Structural Formula (II-B).

In yet another more specific embodiment, for compounds of Structural Formula (II-C), $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl, and values and specific values for the remainder of the variables in Structural Formula (II-C) are as described above for Structural Formula (II-B).

In yet another more specific embodiment, for compounds of Structural Formula (II-C), $R^{1b}$ is hydrogen or optionally substituted methyl, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl, and values and specific values for the remainder of the variables in Structural Formula (II-C) are as described above for Structural Formula (II-B).

In yet another more specific embodiment, for compounds of Structural Formula (II-C), $Cy^1$ is an optionally substituted cyclohexyl, phenyl, pyridyl, pyrimidinyl, thiazolyl, triazolyl, piperidinyl, pyrrolidinyl or benzothiazolyl, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl, and values and specific values for the remainder of the variables in Structural Formula (II-C) are as described above for Structural Formula (II-B).

In yet another more specific embodiment, for compounds of Structural Formula (II-C), $R^{1b}$ is hydrogen or optionally substituted methyl, $Cy^1$ is an optionally substituted cyclohexyl, phenyl, pyridyl, pyrimidinyl, thiazolyl, triazolyl, piperidinyl, pyrrolidinyl or benzothiazolyl, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, imidazopyridinyl, triazolopyridinyl, oxodihydropyridyl, oxodihydropyridazinyl, oxodihydropyrimidinyl or oxodihydropyrrolopyridinyl, and values and specific values for the remainder of the variables in Structural Formula (II-C) are as described above for Structural Formula (II-B).

In a 5th specific embodiment, the compound of the present invention is represented by Structural Formula (II-D):

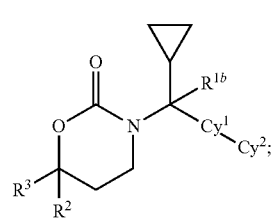

(II-D)

or a pharmaceutically acceptable salt, enantiomer or diastereomer thereof.

The values and specific values for the variables in Structural Formula (II-D) are as described above for Structural Formula (II-C).

In a more specific embodiment, for compounds of Structural Formula (II-D), $Cy^1$ is optionally substituted phenyl, and values and specific values for the remainder of the variables in Structural Formula (II-D) are as described above for Structural Formula (II-C).

In another more specific embodiment, for compounds of Structural Formula (II-D), Cy² is an optionally substituted phenyl, pyridyl, pyridazinyl, pyrimidinyl or oxodihydropyridyl group, and values and specific values for the remainder of the variables in Structural Formula (II-D) are as described above for Structural Formula (II-C).

In another more specific embodiment, for compounds of Structural Formula (II-D), Cy¹ is optionally substituted phenyl, Cy² is an optionally substituted phenyl, pyridyl, pyridazinyl, pyrimidinyl or oxodihydropyridyl group, and values and specific values for the remainder of the variables in Structural Formula (II-D) are as described above for Structural Formula (II-C).

In a 6$^{th}$ specific embodiment, the compound of the present invention is represented by Structural Formula (II-E):

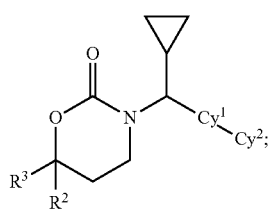

(II-E)

or a pharmaceutically acceptable salt, enantiomer or diastereomer thereof.

The values and specific values for the variables in Structural Formula (II-E) are as described above for Structural Formula (II-D).

In a more specific embodiment, for compounds of Structural Formula (II-E), Cy² is optionally substituted oxodihydropyridyl, and values and specific values for the remainder of the variables in Structural Formula (II-E) are as described above for Structural Formula (II-D).

In a 7$^{th}$ specific embodiment, the compound of the present invention is represented by Structural Formula (II-F):

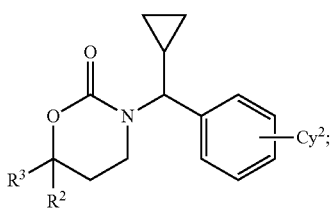

(II-F)

or a pharmaceutically acceptable salt, enantiomer or diastereomer thereof.

The values and specific values for the variables in Structural Formula (II-F) are as described above for Structural Formula (II-E).

In an 8$^{th}$ specific embodiment, the compound of the present invention is represented by Structural Formula (II-G):

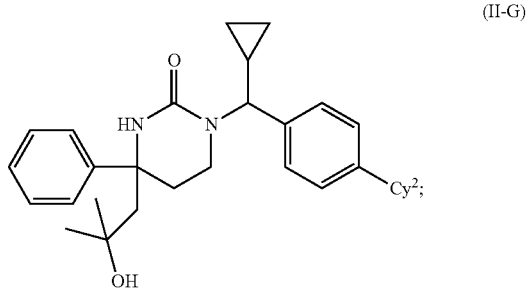

(II-G)

or a pharmaceutically acceptable salt, enantiomer or diastereomer thereof.

Cy² is a pyridyl, pyridazinyl or pyrimidinyl group optionally substituted with methyl, cyclopropyl, cyano, $CONH_2$, CONHMe or $CONMe_2$.

In an alternative specific embodiment, for compounds of Structural Formula (II-G), Cy² is an oxodihydropyridyl group optionally substituted at the ring nitrogen with methyl, ethyl, propyl, isopropyl or cyclopropyl.

In a 9$^{th}$ specific embodiment, the compound of the present invention is represented by Structural Formula (II-H):

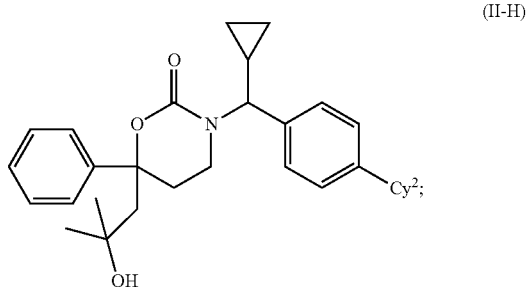

(II-H)

or a pharmaceutically acceptable salt, enantiomer or diastereomer thereof.

Cy² is a pyridyl, pyridazinyl or pyrimidinyl group optionally substituted with methyl, cyclopropyl, cyano, $CONH_2$, CONHMe or $CONMe_2$.

In an alternative specific embodiment, for compounds of Structural Formula (II-H), Cy² is an oxodihydropyridyl group optionally substituted at the ring nitrogen with methyl, ethyl, propyl, isopropyl or cyclopropyl.

In a 10$^{th}$ specific embodiment, the compound of the present invention is represented by Structural Formula (III):

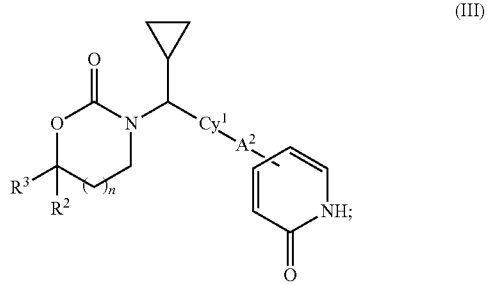

(III)

or a pharmaceutically acceptable salt, enantiomer or diastereomer thereof.

The oxodihydropyridyl ring in formula (III) is independently and optionally substituted on the substitutable ring carbons and/or the ring nitrogen. Exemplary substituents include the groups described as optional substituents for $Cy^2$ as described above for Structural Formula (I). Values and particular values for the remainder of the variables in Structural Formula (III) are as described above for Structural Formula (I).

In a more specific embodiment, for compounds of Structural Formula (III), $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and values and specific values for the remainder of the variables in Structural Formula (III) are as described above for Structural Formula (III).

In an 11<sup>th</sup> specific embodiment, the compound of the present invention is represented by Structural Formula (III-A):

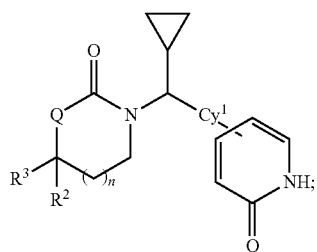

(III-A)

or a pharmaceutically acceptable salt, enantiomer or diastereomer thereof.

The oxodihydropyridyl ring in formula (III-A) is optionally substituted as described above for Structural Formula (III), and the values and particular values for the remainder of the variables in Structural Formula (III-A) are as described above for Structural Formula (III).

In a 12<sup>th</sup> specific embodiment, the compound of the present invention is represented by Structural Formula (III-B):

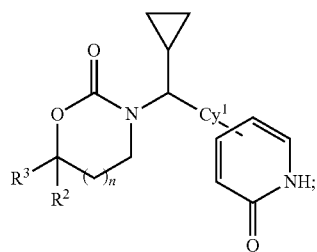

(III-B)

or a pharmaceutically acceptable salt, enantiomer or diastereomer thereof.

The oxodihydropyridyl ring in formula (III-B) is optionally substituted as described above for Structural Formula (III-A), and the values and particular values for the remainder of the variables in Structural Formula (III-B) are as described above for Structural Formula (III-A).

In a 13<sup>th</sup> specific embodiment, the compound of the present invention is represented by Structural Formula (III-C):

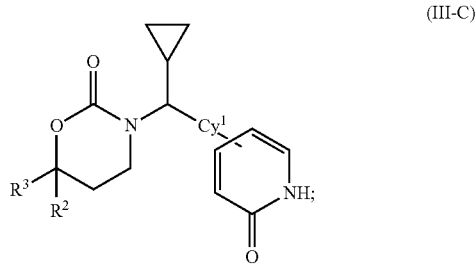

(III-C)

or a pharmaceutically acceptable salt, enantiomer or diastereomer thereof.

The oxodihydropyridyl ring in formula (III-C) is optionally substituted as described above for Structural Formula (III-A), and the values and particular values for the remainder of the variables in Structural Formula (III-C) are as described above for Structural Formula (III-A).

In a more specific embodiment, for compounds of Structural Formula (III-C), $Cy^1$ is an optionally substituted cyclohexyl, phenyl, pyridyl, pyrimidinyl, thiazolyl, triazolyl, piperidinyl, pyrrolidinyl or benzothiazolyl, and values and specific values for the remainder of the variables in Structural Formula (III-C) are as described above for Structural Formula (III-A).

In another more specific embodiment, for compounds of Structural Formula (III-C), $Cy^1$ is optionally substituted phenyl, and values and specific values for the remainder of the variables in Structural Formula (III-C) are as described above for Structural Formula (III-B).

In a 14<sup>th</sup> specific embodiment, the compound of the present invention is represented by Structural Formula (IV):

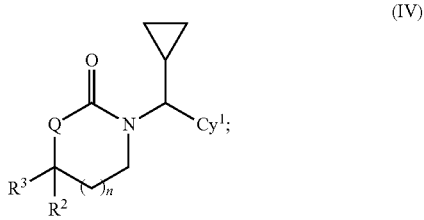

(IV)

or a pharmaceutically acceptable salt, enantiomer or diastereomer thereof.

Values and particular values for the variables in Structural Formula (IV) are as described above for Structural Formula (I).

In a more specific embodiment, for compounds of Structural Formula (IV), $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and values and specific values for the remainder of the variables in Structural Formula (IV) are as described above for Structural Formula (I).

In a 15th specific embodiment, the compound of the present invention is represented by Structural Formula (IV-A):

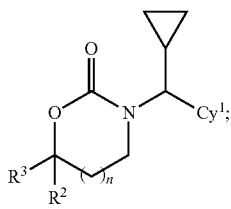

(IV-A)

or a pharmaceutically acceptable salt, enantiomer or diastereomer thereof.

Values and particular values for the variables in Structural Formula (IV-A) are as described above for Structural Formula (IV).

In a 16th specific embodiment, the compound of the present invention is represented by Structural Formula (IV-B):

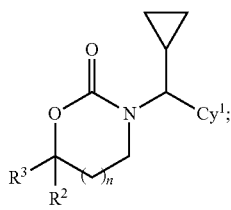

(IV-B)

or a pharmaceutically acceptable salt, enantiomer or diastereomer thereof.

Values and particular values for the variables in Structural Formula (IV-B) are as described above for Structural Formula (IV-A).

In a more specific embodiment, for compounds of Structural Formula (IV-B), $Cy^1$ is an optionally substituted cyclohexyl, phenyl, pyridyl, pyrimidinyl, thiazolyl, triazolyl, piperidinyl, pyrrolidinyl or benzothiazolyl, and values and specific values for the remainder of the variables in Structural Formula (IV-B) are as described above for Structural Formula (IV-A).

In another more specific embodiment, for compounds of Structural Formula (IV-B), $Cy^1$ is optionally substituted phenyl, and values and specific values for the remainder of the variables in Structural Formula (IV-B) are as described above for Structural Formula (IV-A).

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^3$ is ($C_3$-$C_6$)alkenyl, hydroxy($C_2$-$C_5$)alkyl, cyano($C_2$-$C_5$)alkyl, dihydroxy ($C_3$-$C_5$)alkyl, ω-$H_2$NCO($C_1$-$C_5$)alkyl, ($C_1$-$C_2$)alkoxy($C_1$-$C_4$)alkyl, $H_2NSO_2O$($C_2$-$C_5$)alkyl, $H_2NSO_2NH$($C_2$-$C_5$)alkyl, oxo($C_2$-$C_5$)alkyl, MeC(=O)NH($C_2$-$C_5$)alkyl, MeSO$_2$NH ($C_2$-$C_5$)alkyl, or MeSO$_2$NH($C_2$-$C_5$)alkyl, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, $HO_2C$—, $(HO)_2P$(=O)O—, $H_2NS$(=O)$_2$O—, $H_2NS$(=O)$_2NH$—, MeNHC(=O)NH—, MeNHC(=O)O—, oxo, cyano, $HO_2C$—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC=N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N— and MeCONMe, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^2$ is an optionally substituted ($C_1$-$C_6$)alkyl, aryl, heteroaryl or cycloalkyl group; each optionally substituted with up to four groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo ($C_3$-$C_6$)cycloalkyl, halo($C_4$-$C_7$)cycloalkylalkyl, halo($C_1$-$C_6$) alkoxy, halo($C_3$-$C_6$)cycloalkoxy, halo($C_4$-$C_7$) cycloalkylalkoxy, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio and ($C_3$-$C_6$)cycloalkythio;

$R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, $HO_2$C—, $(HO)_2P$(=O)O—, $H_2NS$(=O)$_2$O—, $H_2NS$(=O)$_2$NH—, MeNHC(=O)NH—, MeNHC(=O)O—, oxo, cyano, $HO_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC=N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N— and MeCONMe, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^2$ is an optionally substituted ($C_1$-$C_6$)alkyl, aryl, heteroaryl or cycloalkyl group; each optionally substituted with up to four groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, ($C_3$-$C_6$)cycloalkythio;

$R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, MeNHC(=O)NH—, oxo, cyano, HOCH$_2$C(=O)NH—, EtNHC(=O)NH, MeS—, MeSO$_2$—MeSO$_2$N(Me)-, 2-oxo-1-pyrrolidinyl, H$_2$NCONH—, H$_2$NCO$_2$—, HOCH$_2$CH$_2$O—, MeNH—, Me$_2$N— and MeCONMe, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^2$ is a phenyl, fluorophenyl, isopropyl, cyclopropyl, t-butyl, cyclopropylmethyl or trifluoroethyl, each optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen and cyano;

$R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, MeNHC(=O)NH—, oxo, cyano, HOCH$_2$C(=O)NH—, EtNHC(=O)NH, MeS—, MeSO$_2$—MeSO$_2$N(Me)-, 2-oxo-1-pyrrolidinyl, H$_2$NCONH—, H$_2$NCO$_2$—, HOCH$_2$CH$_2$O—, MeNH—, Me$_2$N— and MeCONMe;

the group represented by Cy$^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl; and the group represented by Cy$^2$ (i.e., oxodihydropyridyl for Structural Formula (III), (III-A), (III-B) and (III-C)), if present, is optionally substituted with 1 to 4 groups independently selected from methyl, ethyl, propyl, cyclopropyl, halo, hydroxy, methoxy, hydroxymethyl, methoxycarbonyl, amino, aminomethyl, cyano, carbamoyl, methylcarbamoyl, dimethylcarbamoyl, (2-methoxyethyl)aminocarbonyl, acetylaminomethyl, methylsulfonyl, acetylaminomethyl, methylsulfonyl, methylsulfonylamino, N-methyl-methylsulfonylamino, methylaminosulfonyl, isopropylaminosulfonyl, dimethylaminosulfonyl, pyrrolidine-1-sulfonyl, methylsulfonylaminomethyldifluoromethyl, trifluoromethyl, 2-fluoroethyl, acetyl, 1-hydroxyethyl, 2-hydroxyethyl and 2-hydroxy-2-propyl, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^2$ is phenyl optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen and cyano;

$R^3$ is 2-methylallyl, MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl;

the group represented by Cy$^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl; and the group represented by Cy$^2$ (i.e., oxodihydropyridyl for Structural Formula (III), (III-A), (III-B) and (III-C)), if present, is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (I), (II), (II-A), (II-B), (II-C), (II-D), (II-E), (II-F), (II-G), (II-H), (III), (III-A), (III-B), (III-C), (IV), (IV-A) or (IV-B), or a pharmaceutically acceptable salt, enantiomer or diastereomer thereof, $R^2$ is phenyl or fluorophenyl;

$R^3$ is 2-methylallyl, 2-hydroxy-2-methylpropyl or 2-cyano-2-methylpropyl; and the groups represented by $Cy^1$ and $Cy^2$ (i.e., oxodihydropyridyl for Structural Formula (III), (III-A), (III-B) and (III-C)), if present, are each, independently, optionally substituted with fluoro, chloro, bromo, cyano, $CONH_2$, $CONHMe$, $CONMe_2$, methyl, ethyl, cyclopropyl, $OCHF_2$, $CHF_2$, $CHF_2CH_2$ or $CF_3$, and values and particular or specific values for the remainder of the variables in Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively, are as described above for Structural Formula (I), (II), (II-A), (II-B), (II-C), (II-D), (II-E), (II-F), (II-G), (II-H), (III), (III-A), (III-B), (III-C), (IV), (IV-A) or (IV-B), respectively.

In another embodiment of the present invention, for a compound of Structural Formula (III), (III-A), (III-B) or (III-C), or a pharmaceutically acceptable salt, enantiomer or diastereomer thereof, $R^2$ is phenyl or fluorophenyl;

$R^3$ is 2-methylallyl, 2-hydroxy-2-methylpropyl or 2-cyano-2-methylpropyl; and the group represented by $Cy^1$ is optionally substituted with fluoro, chloro, bromo, methyl, ethyl, cyclopropyl, $OCHF_2$ or $CF_3$; and the oxodihydropyridyl ring in structural formulas (III) to (III-C) is optionally substituted at the ring nitrogen with methyl, ethyl, propyl, cyclopropyl, difluoromethyl or 2-fluoroethyl, and values and particular or specific values for the remainder of the variables in Structural Formula (III), (III-A), (III-B) or (III-C), respectively, are as described above for Structural Formula (III), (III-A), (III-B) or (III-C), respectively.

Preferred values for the variables in the above-described Structural Formula (I), (II), (II-A), (II-B), (II-C), (II-D), (II-E), (II-F), (II-G), (II-H), (III), (III-A), (III-B), (III-C), (IV), (IV-A) and (IV-B) are provided below:

Q is O or $CH_2$ and n is 1. Alternatively, Q is O or $NR^5$ and n is 1. Alternatively, Q is O or NH and n is 1. Alternatively, Q is O and n is 1. Alternatively, Q is O or $CH_2$, E is a bond and n is 1. Alternatively, Q is O or $NR^5$, E is a bond and n is 1. Alternatively, Q is O or NH, E is a bond and n is 1. Alternatively, Q is O, E is a bond and n is 1. Alternatively, E is a bond and n is 1. Alternatively, Q is O or $NR^5$ and E is a bond. Alternatively, Q is O or NH and E is a bond. Alternatively, Q is O and E is a bond. Alternatively, Q is O or $CH_2$, n is 1 and $A^1$ is a bond. Alternatively, Q is O or $NR^5$, n is 1 and $A^1$ is a bond. Alternatively, Q is O or NH, n is 1 and $A^1$ is a bond. Alternatively, Q is O, n is 1 and $A^1$ is a bond. Alternatively, Q is O or $CH_2$, E is a bond, n is 1 and $A^1$ is a bond. Alternatively, Q is O or $NR^5$, E is a bond, n is 1 and $A^1$ is a bond. Alternatively, Q is O or NH, E is a bond, n is 1 and $A^1$ is a bond. Alternatively, Q is O, E is a bond, n is 1 and $A^1$ is a bond. Alternatively, E is a bond, n is 1 and $A^1$ is a bond. Alternatively, Q is O or $NR^5$, E is a bond and $A^1$ is a bond. Alternatively, Q is O or NH, E is a bond and $A^1$ is a bond. Alternatively, Q is O, E is a bond and $A^1$ is a bond. Alternatively, Q is O or $CH_2$, n is 1 and $A^2$ is a bond. Alternatively, Q is O or $NR^5$, n is 1 and $A^2$ is a bond. Alternatively, Q is O or NH, n is 1 and $A^2$ is a bond. Alternatively, Q is O, n is 1 and $A^2$ is a bond. Alternatively, Q is O or $CH_2$, E is a bond, n is 1 and $A^2$ is a bond. Alternatively, Q is O or $NR^5$, E is a bond, n is 1 and $A^2$ is a bond. Alternatively, Q is O or NH, E is a bond, n is 1 and $A^2$ is a bond. Alternatively, Q is O, E is a bond, n is 1 and $A^2$ is a bond. Alternatively, E is a bond, n is 1 and $A^2$ is a bond. Alternatively, Q is O or $NR^5$, E is a bond and $A^2$ is a bond. Alternatively, Q is O or NH, E is a bond and $A^2$ is a bond. Alternatively, Q is O, E is a bond and $A^2$ is a bond. Alternatively, Q is O or $CH_2$, n is 1, $A^1$ is a bond and $A^2$ is a bond. Alternatively, Q is O or $NR^5$, n is 1, $A^1$ is a bond and $A^2$ is a bond. Alternatively, Q is O or NH, n is 1, $A^1$ is a bond and $A^2$ is a bond. Alternatively, Q is O, n is 1, $A^1$ is a bond and $A^2$ is a bond. Alternatively, Q is O or $CH_2$, E is a bond, n is 1, $A^1$ is a bond and $A^2$ is a bond. Alternatively, Q is O or $NR^5$, E is a bond, n is 1, $A^1$ is a bond and $A^2$ is a bond. Alternatively, Q is O or NH, E is a bond, n is 1, $A^1$ is a bond and $A^2$ is a bond. Alternatively, Q is O, E is a bond, n is 1, $A^1$ is a bond and $A^2$ is a bond. Alternatively, E is a bond, n is 1, $A^1$ is a bond and $A^2$ is a bond. Alternatively, Q is O or $NR^5$, E is a bond, $A^1$ is a bond and $A^2$ is a bond. Alternatively, Q is O or NH, E is a bond, $A^1$ is a bond and $A^2$ is a bond. Alternatively, Q is O, E is a bond, $A^1$ is a bond and $A^2$ is a bond. Alternatively, Q is O, $A^1$ is a bond and $A^2$ is a bond.

$R^{1a}$ is optionally substituted $(C_3-C_7)$cycloalkyl and $R^{1b}$ is H or optionally substituted $(C_1-C_6)$alkyl. Alternatively, $R^{1a}$ is optionally substituted $(C_3-C_7)$cycloalkyl and $R^{1b}$ is H or an optionally substituted methyl, ethyl, or propyl group. Alternatively, $R^{1a}$ is optionally substituted $(C_3-C_5)$cycloalkyl and $R^{1b}$ is H or optionally substituted $(C_1-C_6)$alkyl. Alternatively, $R^{1a}$ is optionally substituted $(C_3-C_5)$cycloalkyl and $R^{1b}$ is H or an optionally substituted methyl, ethyl, or propyl group. Alternatively, $R^{1a}$ is optionally substituted cyclopropyl and $R^{1b}$ is H or optionally substituted $(C_1-C_6)$alkyl. Alternatively, $R^{1a}$ is optionally substituted cyclopropyl and $R^{1b}$ is H or an optionally substituted methyl, ethyl, or propyl group. Alternatively, $R^{1a}$ is optionally substituted $(C_3-C_7)$cycloalkyl and $R^{1b}$ is H. Alternatively, $R^{1a}$ is optionally substituted $(C_3-C_5)$cycloalkyl and $R^{1b}$ is H. Alternatively, $R^{1a}$ is optionally substituted cyclopropyl and $R^{1b}$ is H. Alternatively, $R^{1a}$ is optionally substituted $(C_3-C_7)$cycloalkyl and $R^{1b}$ is H or optionally substituted $(C_1-C_6)$alkyl, and the groups represented by $R^{1a}$ and $R^{1b}$ are independently optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—. Alternatively, $R^{1a}$ is optionally substituted $(C_3-C_7)$cycloalkyl and $R^{1b}$ is H or an optionally substituted methyl, ethyl, or propyl group, and the groups represented by $R^{1a}$ and $R^{1b}$ are independently optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—. Alternatively, $R^{1a}$ is optionally substituted $(C_3-C_5)$cycloalkyl and $R^{1b}$ is H or optionally substituted $(C_1-C_6)$alkyl, and the groups represented by $R^{1a}$ and $R^{1b}$ are independently optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$. Alternatively, $R^{1a}$ is optionally substituted $(C_3-C_5)$cycloalkyl and $R^{1b}$ is H or an optionally substituted methyl, ethyl, or propyl group, and the groups represented by $R^{1a}$ and $R^{1b}$ are independently optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—. Alternatively, $R^{1a}$ is optionally substituted cyclopropyl and $R^{1b}$ is H or optionally substituted $(C_1-C_6)$alkyl, and the groups represented by $R^{1a}$ and $R^{1b}$ are independently optionally substituted with up to four groups independently selected from fluorine, cyano, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl, $(C_1$-$C_6)$alkoxy$(C_1$-$C_6)$alkyl and $R^4O$. Alternatively, $R^{1a}$ is optionally substituted cyclopropyl and $R^{1b}$ is H or an optionally substituted methyl, ethyl, or propyl group, and the groups represented by $R^{1a}$ and $R^{1b}$ are independently optionally substituted with up to four groups independently selected from fluorine, cyano, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl, $(C_1$-$C_6)$alkoxy$(C_1$-$C_6)$alkyl and $R^4O$—. Alternatively, $R^{1a}$ is optionally substituted $(C_3$-$C_7)$cycloalkyl and $R^{1b}$ is H, and the groups represented by $R^{1a}$ and $R^{1b}$ are independently optionally substituted with up to four groups independently selected from fluorine, cyano, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl, $(C_1$-$C_6)$alkoxy$(C_1$-$C_6)$alkyl and $R^4O$. Alternatively, $R^{1a}$ is optionally substituted $(C_3$-$C_5)$cycloalkyl and $R^{1b}$ is H, and the group represented by $R^{1a}$ is optionally substituted with up to four groups independently selected from fluorine, cyano, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl, $(C_1$-$C_6)$alkoxy$(C_1$-$C_6)$alkyl and $R^4O$—. Alternatively, $R^{1a}$ is optionally substituted cyclopropyl and $R^{1b}$ is H, and the group represented by $R^{1a}$ is optionally substituted with up to four groups independently selected from fluorine, cyano, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl, $(C_1$-$C_6)$alkoxy$(C_1$-$C_6)$alkyl and $R^4O$—. Alternatively, $R^{1a}$ is unsubstituted $(C_3$-$C_7)$cycloalkyl and $R^{1b}$ is H or unsubstituted $(C_1$-$C_6)$alkyl. Alternatively, $R^{1a}$ is unsubstituted $(C_3$-$C_7)$cycloalkyl and $R^{1b}$ is H or an unsubstituted methyl, ethyl, or propyl group. Alternatively, $R^{1a}$ is unsubstituted $(C_3$-$C_5)$cycloalkyl and $R^{1b}$ is H or unsubstituted $(C_1$-$C_6)$alkyl. Alternatively, $R^{1a}$ is unsubstituted $(C_3$-$C_5)$cycloalkyl and $R^{1b}$ is H or an unsubstituted methyl, ethyl, or propyl group. Alternatively, $R^{1a}$ is unsubstituted cyclopropyl and $R^{1b}$ is H or unsubstituted $(C_1$-$C_6)$alkyl. Alternatively, $R^{1a}$ is unsubstituted cyclopropyl and $R^{1b}$ is H or an unsubstituted methyl, ethyl, or propyl group. Alternatively, $R^{1a}$ is unsubstituted $(C_3$-$C_7)$cycloalkyl and $R^{1b}$ is H. Alternatively, $R^{1a}$ is unsubstituted $(C_3$-$C_5)$cycloalkyl and $R^{1b}$ is H. Alternatively, $R^{1a}$ is unsubstituted cyclopropyl and $R^{1b}$ is H.

$Cy^1$ is an optionally substituted aryl, heteroaryl, monocyclic cycloalkyl or monocyclic heterocyclyl group and $Cy^2$ is an optionally substituted aryl, heteroaryl, cycloalkyl or heterocyclyl group. Alternatively, $Cy^1$ is an optionally substituted aryl or heteroaryl group. Alternatively, $Cy^1$ is an optionally substituted aryl. Alternatively, $Cy^1$ is an optionally substituted aryl or heteroaryl group and $Cy^2$ is an optionally substituted aryl, heteroaryl, cycloalkyl or heterocyclyl group. Alternatively, $Cy^1$ is an optionally substituted aryl and $Cy^2$ is an optionally substituted aryl, heteroaryl, cycloalkyl or heterocyclyl group. Alternatively, $Cy^1$ is an optionally substituted aryl, heteroaryl, monocyclic cycloalkyl or monocyclic heterocyclyl group and $Cy^2$ is an optionally substituted aryl or heteroaryl group. Alternatively, $Cy^1$ is an optionally substituted aryl or heteroaryl group and $Cy^2$ is an optionally substituted aryl or heteroaryl group. Alternatively, $Cy^1$ is an optionally substituted aryl and $Cy^2$ is an optionally substituted aryl or heteroaryl group. Alternatively, $Cy^1$ is an optionally substituted aryl and $Cy^2$ is an optionally substituted aryl. Alternatively, $Cy^1$ is an optionally substituted aryl, heteroaryl, monocyclic cycloalkyl or monocyclic heterocyclyl group and $Cy^2$ is H. Alternatively, $Cy^1$ is an optionally substituted aryl or heteroaryl group and $Cy^2$ is H. Alternatively, $Cy^1$ is an optionally substituted aryl and $Cy^2$ is H. $Cy^1$ is an optionally substituted phenyl and $Cy^2$ is an optionally substituted aryl, heteroaryl, cycloalkyl or heterocyclyl group. Alternatively, $Cy^1$ is an optionally substituted phenyl and $Cy^2$ is an optionally substituted aryl or heteroaryl group. Alternatively, $Cy^1$ is an optionally substituted phenyl and $Cy^2$ is an optionally substituted aryl. Alternatively, $Cy^1$ is an optionally substituted phenyl and $Cy^2$ is an optionally substituted aryl. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl, heteroaryl, cycloalkyl or heterocyclyl group. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl or heteroaryl group. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl. $Cy^1$ is an optionally substituted aryl and $Cy^2$ is an optionally substituted phenyl, pyridyl, pyridazinyl, pyrimidinyl or oxodihydropyridyl group. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted phenyl, pyridyl, pyridazinyl, pyrimidinyl or oxodihydropyridyl group. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted oxodihydropyridyl group. Alternatively, $Cy^1$ is an optionally substituted phenyl and $Cy^2$ is an optionally substituted phenyl, pyridyl, pyridazinyl, pyrimidinyl or oxodihydropyridyl group. Alternatively, $Cy^1$ is an optionally substituted phenyl and $Cy^2$ is an optionally substituted oxodihydropyridyl group. Alternatively, $Cy^1$ is an optionally substituted phenyl and $Cy^2$ is an optionally substituted pyridyl group. Alternatively, $Cy^1$ is an optionally substituted phenyl and $Cy^2$ is an optionally substituted pyridazinyl group. Alternatively, $Cy^1$ is an optionally substituted phenyl and $Cy^2$ is an optionally substituted pyrimidinyl group. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted phenyl, pyridyl, pyridazinyl, pyrimidinyl or oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the oxodihydropyridyl group is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $Cy^1$ is an optionally substituted phenyl, $Cy^2$ is an optionally substituted phenyl, pyridyl, pyridazinyl, pyrimidinyl or oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the oxodihydropyridyl group is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $Cy^1$ is an optionally substituted phenyl and $Cy^2$ is an optionally substituted oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the oxodihydropyridyl group is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted phenyl, pyridyl, pyridazinyl, pyrimidinyl or oxodihydropyridyl group, and the groups represented by $Cy^1$ and $Cy^2$ are each, independently, optionally substituted with fluoro, chloro, bromo, cyano, $CONH_2$, CONHMe, $CONMe_2$, methyl, ethyl, cyclopropyl, $OCHF_2$, $CHF_2$, $CHF_2CH_2$ or $CF_3$. Alternatively, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted oxodihydropyridyl group, the group represented by $Cy^1$ is optionally substituted with fluoro, chloro, bromo, methyl, ethyl, cyclopropyl, $OCHF_2$, $CHF_2$ or $CF_3$, and the oxodihydropyridyl is optionally substituted at the ring nitrogen with methyl, ethyl, propyl, cyclopropyl, difluoromethyl, 2-fluoroethyl or 2,2,2-trifluoroethyl. Alternatively, $Cy^1$ is an optionally substituted phenyl, $Cy^2$ is an optionally substituted phenyl, pyridyl, pyridazinyl, pyrimidinyl or oxodihydropyridyl group, and the groups represented by $Cy^1$ and $Cy^2$ are each, independently, optionally substituted with fluoro, chloro, bromo, cyano, $CONH_2$, CONHMe, $CONMe_2$, methyl, ethyl, cyclopropyl, $OCHF_2$, $CHF_2$, $CHF_2CH_2$ or $CF_3$. Alternatively, $Cy^1$ is an optionally substituted phenyl and $Cy^2$ is an optionally substituted oxodihydropyridyl group, and the group represented by $Cy^1$ is optionally substituted with fluoro, chloro, bromo, methyl, ethyl, cyclopropyl, $OCHF_2$, or $CF_3$, and the oxodihydropyridyl is optionally substituted at the ring nitrogen with methyl, ethyl, propyl, cyclopropyl, difluoromethyl, 2-fluoroethyl or 2,2,2-trifluoroethyl.

Alternatively, $A^2$ is a bond, $Cy^1$ is an optionally substituted aryl, heteroaryl, monocyclic cycloalkyl or monocyclic heterocyclyl group and $Cy^2$ is an optionally substituted aryl, heteroaryl, cycloalkyl or heterocyclyl group. Alternatively, $A^2$ is a bond, $Cy^1$ is an optionally substituted aryl or heteroaryl group. Alternatively, $A^2$ is a bond, $Cy^1$ is an optionally substituted aryl. Alternatively, $A^2$ is a bond, $Cy^1$ is an optionally substituted aryl or heteroaryl group and $Cy^2$ is an optionally substituted aryl, heteroaryl, cycloalkyl or heterocyclyl group. Alternatively, $A^2$ is a bond, $Cy^1$ is an optionally substituted aryl and $Cy^2$ is an optionally substituted aryl, heteroaryl, cycloalkyl or heterocyclyl group. Alternatively, $A^2$ is a bond, $Cy^1$ is an optionally substituted aryl, heteroaryl, monocyclic cycloalkyl or monocyclic heterocyclyl group and $Cy^2$ is an optionally substituted aryl or heteroaryl group. Alternatively, $A^2$ is a bond, $Cy^1$ is an optionally substituted aryl or heteroaryl group and $Cy^2$ is an optionally substituted aryl or heteroaryl group. Alternatively, $A^2$ is a bond, $Cy^1$ is an optionally substituted aryl and $Cy^2$ is an optionally substituted aryl or heteroaryl group. Alternatively, $A^2$ is a bond, $Cy^1$ is an optionally substituted aryl and $Cy^2$ is an optionally substituted aryl. Alternatively, $A^2$ is a bond, $Cy^1$ is an optionally substituted aryl, heteroaryl, monocyclic cycloalkyl or monocyclic heterocyclyl group and $Cy^2$ is H. Alternatively, $A^2$ is a bond, $Cy^1$ is an optionally substituted aryl or heteroaryl group and $Cy^2$ is H. Alternatively, $A^2$ is a bond, $Cy^1$ is an optionally substituted aryl and $Cy^2$ is H. $Cy^1$ is an optionally substituted phenyl and $Cy^2$ is an optionally substituted aryl, heteroaryl, cycloalkyl or heterocyclyl group. Alternatively, $A^2$ is a bond, $Cy^1$ is an optionally substituted phenyl and $Cy^2$ is an optionally substituted aryl or heteroaryl group. Alternatively, $A^2$ is a bond, $Cy^1$ is an optionally substituted phenyl and $Cy^2$ is an optionally substituted aryl. Alternatively, $A^2$ is a bond, $Cy^1$ is an optionally substituted phenyl and $Cy^2$ is an optionally substituted aryl. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl, heteroaryl, cycloalkyl or heterocyclyl group. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl or heteroaryl group. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted aryl. $Cy^1$ is an optionally substituted aryl and $Cy^2$ is an optionally substituted phenyl, pyridyl, pyridazinyl, pyrimidinyl or oxodihydropyridyl group. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted phenyl, pyridyl, pyridazinyl, pyrimidinyl or oxodihydropyridyl group. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group and $Cy^2$ is an optionally substituted oxodihydropyridyl group. Alternatively, $A^2$ is a bond, $Cy^1$ is an optionally substituted phenyl and $Cy^2$ is an optionally substituted phenyl, pyridyl, pyridazinyl, pyrimidinyl or oxodihydropyridyl group. Alternatively, $A^2$ is a bond, $Cy^1$ is an optionally substituted phenyl and $Cy^2$ is an optionally substituted oxodihydropyridyl group. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted phenyl, pyridyl, pyridazinyl, pyrimidinyl or oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the oxodihydropyridyl group is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $A^2$ is a bond, $Cy^1$ is an optionally substituted phenyl, $Cy^2$ is an optionally substituted phenyl, pyridyl, pyridazinyl, pyrimidinyl or oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the oxodihydropyridyl group is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $A^2$ is a bond, $Cy^1$ is an optionally substituted phenyl and $Cy^2$ is an optionally substituted oxodihydropyridyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxymethyl, 2-hydroxyethyl, 2-hydroxy-2-propyl, methoxymethyl, methylsulfonyl, methylsulfonylamino, N-methyl-methylsulfonylamino and benzyloxycarbonyl, and the oxodihydropyridyl group is optionally substituted with 1 to 4 groups independently selected from methyl, ethyl, propyl, cyclopropyl, halo, hydroxy, methoxy, hydroxymethyl, methoxycarbonyl, amino, cyano, carbamoyl, methylcarbamoyl, dimethylcarbamoyl, methylsulfonyl, methylsulfonylamino, N-methyl-methylsulfonylamino difluoromethyl, trifluoromethyl, 2-fluoroethyl, acetyl, 1-hydroxyethyl, 2-hydroxyethyl and 2-hydroxy-2-propyl. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted phenyl, pyridyl, pyridazinyl, pyrimidinyl or oxodihydropyridyl group, and the groups represented by $Cy^1$ and $Cy^2$ are each, independently, optionally substituted with fluoro, chloro, bromo, cyano, $CONH_2$, CONHMe, $CONMe_2$, methyl, ethyl, cyclopropyl, $OCHF_2$, $CHF_2$, $CHF_2CH_2$ or $CF_3$. Alternatively, $A^2$ is a bond, $Cy^1$ is an optionally substituted cyclohexyl, phenyl, pyridyl, pyrimidinyl, thiazolyl, triazolyl, piperidinyl, pyrrolidinyl or benzothiazolyl group, $Cy^2$ is an optionally substituted oxodihydropyridyl group, and the group represented by $Cy^1$ is optionally substituted with fluoro, chloro, bromo, methyl, ethyl, cyclopropyl, $OCHF_2$ or $CF_3$, and the oxodihydropyridyl is optionally substituted at the ring nitrogen with methyl, ethyl, propyl, cyclopropyl, difluoromethyl, 2-fluoroethyl or 2,2,2-trifluoroethyl. Alternatively, $A^2$ is a bond, $Cy^1$ is an optionally substituted phenyl, $Cy^2$ is an optionally substituted phenyl, pyridyl, pyridazinyl, pyrimidinyl or oxodihydropyridyl group, and the groups represented by $Cy^1$ and $Cy^2$ are each, independently, optionally substituted with fluoro, chloro, bromo, cyano, $CONH_2$, CONHMe, $CONMe_2$, methyl, ethyl, cyclopropyl, $OCHF_2$, $CHF_2$, $CHF_2CH_2$ or $CF_3$. Alternatively, $A^2$ is a bond, $Cy^1$ is an optionally substituted phenyl and $Cy^2$ is an optionally substituted oxodihydropyridyl group, the group represented by $Cy^1$ is optionally substituted with fluoro, chloro, bromo, methyl, ethyl, cyclopropyl, $OCHF_2$ or $CF_3$, and the oxodihydropyridyl is optionally substituted at the ring nitrogen with methyl, ethyl, propyl, cyclopropyl, difluoromethyl, 2-fluoroethyl or 2,2,2-trifluoroethyl.

$R^2$ is an optionally substituted $(C_1-C_6)$alkyl, aryl, heteroaryl, cycloalkyl or heterocyclyl group. Alternatively, $R^2$ is an optionally substituted methyl, ethyl, propyl, butyl, aryl, heteroaryl, cycloalkyl or heterocyclyl group. Alternatively, $R^2$ is an optionally substituted aryl, heteroaryl, cycloalkyl or heterocyclyl group. Alternatively, $R^2$ is an optionally substituted aryl group. Alternatively, $R^2$ is an optionally substituted phenyl, fluorophenyl, isopropyl, cyclopropyl, t-butyl, cyclopropylmethyl or trifluoroethyl group. Alternatively, $R^2$ is an optionally substituted phenyl or fluorophenyl group. Alternatively, $R^2$ is an unsubstituted phenyl or fluorophenyl group.

Alternatively, $R^2$ is an optionally substituted $(C_1-C_6)$alkyl, aryl, heteroaryl or cycloalkyl group, each group optionally substituted with up to four groups independently selected from halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio and $(C_3-C_6)$cycloalkythio.

Alternatively, $R^2$ is an optionally substituted aryl, heteroaryl or cycloalkyl group, each group optionally substituted with up to four groups independently selected from halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio and $(C_3-C_6)$cycloalkythio.

Alternatively, $R^2$ is an aryl group optionally substituted with up to four groups independently selected from halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio and $(C_3-C_6)$cycloalkythio.

Alternatively, $R^2$ is a phenyl group optionally substituted with up to four groups independently selected from halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio and $(C_3-C_6)$cycloalkythio.

Alternatively, $R^2$ is an aryl group optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen and cyano. Alternatively, $R^2$ is a phenyl, fluorophenyl, isopropyl, cyclopropyl, t-butyl, cyclopropylmethyl or trifluoroethyl group, each optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen and cyano. Alternatively, $R^2$ is a phenyl or fluorophenyl group, each optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen and cyano.

$R^3$ is an optionally substituted $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl group. Alternatively, $R^3$ is an optionally substituted $(C_1-C_6)$ alkyl. Alternatively, $R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe. Alternatively, $R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, MeNHC(=O)NH—, oxo, cyano, HOCH$_2$C(=O)NH—, EtNHC(=O)NH, MeS—, MeSO$_2$-MeSO$_2$N(Me)-, 2-oxo-1-pyrrolidinyl, H$_2$NCONH—, H$_2$NCO$_2$—, HOCH$_2$CH$_2$O—, MeNH—, Me$_2$N— and MeCONMe. Alternatively, $R^3$ is $(C_3-C_6)$alkenyl, hydroxy$(C_2-C_5)$alkyl, cyano$(C_2-C_5)$alkyl, dihydroxy$(C_3-C_5)$alkyl, ω-H$_2$NCO$(C_1-C_5)$alkyl, $(C_1-C_2)$alkoxy$(C_1-C_4)$alkyl, H$_2$NSO$_2$O$(C_2-C_5)$alkyl, H$_2$NSO$_2$NH$(C_2-C_5)$alkyl, oxo$(C_2-C_5)$alkyl, MeC(=O)NH$(C_2-C_5)$alkyl, MeSO$_2$NH$(C_2-C_5)$alkyl, or MeSO$_2$NH$(C_2-C_5)$alkyl. Alternatively, $R^3$ is 2-methylallyl, MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl. Alternatively, $R^3$ is 2-methylallyl, 2-hydroxy-2-methylpropyl or 2-cyano-2-methylpropyl. Alternatively, $R^3$ is an optionally substituted $(C_1-C_6)$ alkyl, and $R^2$ is an optionally substituted aryl, heteroaryl, cycloalkyl or heterocyclyl group. Alternatively, $R^3$ is an optionally substituted $(C_1-C_6)$ alkyl, and $R^2$ is an optionally substituted aryl group. Alternatively, $R^3$ is an optionally substituted $(C_1-C_6)$ alkyl, and $R^2$ is an optionally substituted phenyl, fluorophenyl, isopropyl, cyclopropyl, t-butyl, cyclopropylmethyl or trifluoroethyl group. Alternatively, $R^3$ is $(C_3-C_6)$alkenyl, hydroxy$(C_2-C_5)$alkyl, cyano$(C_2-C_5)$alkyl, dihydroxy$(C_3-C_5)$alkyl, ω-H$_2$NCO$(C_1-C_5)$alkyl, $(C_1-C_2)$alkoxy$(C_1-C_4)$alkyl, H$_2$NSO$_2$O$(C_2-C_5)$alkyl, H$_2$NSO$_2$NH$(C_2-C_5)$alkyl, oxo$(C_2-C_5)$alkyl, MeC(=O)NH$(C_2-C_5)$alkyl, MeSO$_2$NH$(C_2-C_5)$alkyl, or MeSO$_2$NH$(C_2-C_5)$alkyl, and $R^2$ is an aryl group optionally substituted with up to four groups independently selected from halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl ($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio and ($C_3$-$C_6$)cycloalkythio. Alternatively, $R^3$ is ($C_3$-$C_6$)alkenyl, hydroxy($C_2$-$C_5$)alkyl, cyano($C_2$-$C_5$)alkyl, dihydroxy($C_3$-$C_5$)alkyl, ω-$H_2$NCO($C_1$-$C_5$)alkyl, ($C_1$-$C_2$)alkoxy($C_1$-$C_4$)alkyl, $H_2$NSO$_2$O($C_2$-$C_5$)alkyl, $H_2$NSO$_2$NH($C_2$-$C_5$)alkyl, oxo($C_2$-$C_5$)alkyl, MeC(=O)NH($C_2$-$C_5$)alkyl, MeSO$_2$NH($C_2$-$C_5$)alkyl, or MeSO$_2$NH($C_2$-$C_5$)alkyl, and $R^2$ is a phenyl group optionally substituted with up to four groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio and ($C_3$-$C_6$)cycloalkythio. Alternatively, $R^3$ is ($C_3$-$C_6$)alkenyl, hydroxy($C_2$-$C_5$)alkyl, cyano($C_2$-$C_5$)alkyl, dihydroxy($C_3$-$C_5$)alkyl, ω-$H_2$NCO($C_1$-$C_5$)alkyl, ($C_1$-$C_2$)alkoxy($C_1$-$C_4$)alkyl, $H_2$NSO$_2$O($C_2$-$C_5$)alkyl, $H_2$NSO$_2$NH($C_2$-$C_5$)alkyl, oxo($C_2$-$C_5$)alkyl, MeC(=O)NH($C_2$-$C_5$)alkyl, MeSO$_2$NH($C_2$-$C_5$)alkyl, or MeSO$_2$NH($C_2$-$C_5$)alkyl, and $R^2$ is a phenyl or fluorophenyl group, each optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen and cyano. Alternatively, $R^3$ is 2-methylallyl, MeSO$_2$NHCH$_2$CH$_2$CH$_2$, $H_2$NC(=O)CH$_2$CH$_2$, $H_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl, and $R^2$ is an aryl group optionally substituted with up to four groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio and ($C_3$-$C_6$)cycloalkythio. Alternatively, $R^3$ is 2-methylallyl, MeSO$_2$NHCH$_2$CH$_2$CH$_2$, $H_2$NC(=O)CH$_2$CH$_2$, $H_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl, and $R^2$ is a phenyl group optionally substituted with up to four groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio and ($C_3$-$C_6$)cycloalkythio. Alternatively, $R^3$ is 2-methylallyl, MeSO$_2$NHCH$_2$CH$_2$CH$_2$, $H_2$NC(=O)CH$_2$CH$_2$, $H_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl, and $R^2$ is a phenyl or fluorophenyl group, each optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen and cyano. Alternatively, $R^3$ is 2-methylallyl, 2-hydroxy-2-methylpropyl or 2-cyano-2-methylpropyl, and $R^2$ is a phenyl group optionally substituted with up to four groups independently selected from halogen, —CN, —NO$_2$, —NH$_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio and ($C_3$-$C_6$)cycloalkythio. Alternatively, $R^3$ is 2-methylallyl, 2-hydroxy-2-methylpropyl or 2-cyano-2-methylpropyl, and $R^2$ is a phenyl or fluorophenyl group, each optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen and cyano.

Definitions

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

"Alkynyl" is an alkyl group in which at least one carbon-carbon bond has been replaced with a triple bond.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro [4.4]nonane, adamantyl and the like.

The term "aryl" means an carbocyclic aromatic radical with six to fourteen carbon atoms. Examples include phenyl, a naphthyl, indanyl or a tetrahydronaphthalene. A substituted aryl group has 1-4 substituents. Unless otherwise indicated, exemplary substituents include alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido. The term "aryl" may be used interchangeably with the terms "aryl ring" "carbocyclic aromatic ring", "aryl group" and "carbocyclic aromatic group".

The term "heteroaryl" means a 5- and 12-membered heteroaromatic radical containing 0-4 heteroatoms selected from N, O, and S. A heteroaryl can be moncyclic or bicyclic, for example, fused to an aryl, moncyclic heteroaryl, heterocyclyl or cycloalkyl group. Examples include 2- or 3-thienyl, 2- or 3-furanyl, 2- or 3- pyrrolyl, 2-,3-, or 4-pyridyl, 2-pyrazinyl, 2-, 4-, or 5-pyrimidinyl, 3- or 4-pyridazinyl, 1H-indol-6-yl, 1H-indol-5-yl, 1 H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A substituted heteroaryl has from 1-4 substituents. Unless otherwise indicated, exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide. The term "heteroaryl", "heteroaromatic", "heteroaryl ring", "heteroaryl group", "heteroaromatic ring", and "heteroaromatic group" are used interchangeably.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine- 2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A substituted heterocyclyl has 1-4 substituents. Unless otherwise indicated, exemplary substituents include alkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "compound" also includes labeling at one or more positions with deuterium. "Labeled with deuterium at a position" means that the amount deuterium at the position is greater than the amount that is present at natural abundance. In certain instances, the deuterium at each position in a "compound" is at natural abundance.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers, i.e., stereochemically pure. "Stereochemical purity" is the weight of the stereoisomer divided by the combined weight of all of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer divided by the combined weight of the enantiomer and the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
| --- | --- |
| A% | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| dppf | 1,1'-Bis(diphenylphosphino)ferrocene |
| DPTBS | Diphenyl-t-butylsilyl |
| dr | diastereomer ratio |
| EDC. HCl, EDCl | 1[3-(dimethylamino)propyl]-3-ethylcarbodiimide hydrochloride |
| Equiv | equivalents |
| EtOAc | Ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I can be prepared by several processes. In the discussion below, $A^1$, $A^2$, E, Q, $Cy^1$, $Cy^2$, $R^1$, $R^2$, $R^3$, and n have the meanings specified above unless otherwise noted. In cases where the synthetic intermediates and final products of Formula I described below contain potentially reactive functional groups such as amino, hydroxyl, thiol and carboxy that may interfere with the desired reaction it may be advantageous to employ protected or masked forms of the respective group. Methods for the selection, introduction and removal of protecting groups are well known to those skilled in the art (see e.g. T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are preferably used in equimolar amounts, however, in certain cases it may be beneficial to use an excess of one reagent to drive the reaction to completion. This is especially the case when the excess reagent can be readily removed by evaporation or extraction.

In a first process a compound of Formula I, wherein Q denotes O or $NR^5$, can be prepared by reaction of an aminoalcohol (Q=O) or a diamine (Q=$NR^5$) intermediate of Formula 2 with a reagent of Formula 3, wherein $Z^1$ and $Z^2$ are leaving groups such as chloride, 1-imidazolyl or aryloxide in an inert solvent such as tetrahydrofuran, $CH_2Cl_2$, 1,4-dioxane, toluene or MeCN, preferably in the presence of an organic or inorganic base such as triethylamine, pyridine, or $NaHCO_3$, optionally in the presence of an additive such as 4-dimethylaminopyridine, at −10° C. to 120° C. Commercially available compounds 3 such as phosgene, diphosgene, triphosgene, carbonyl diimidazole, p-nitrophenyl chloroformate are particularly preferred.

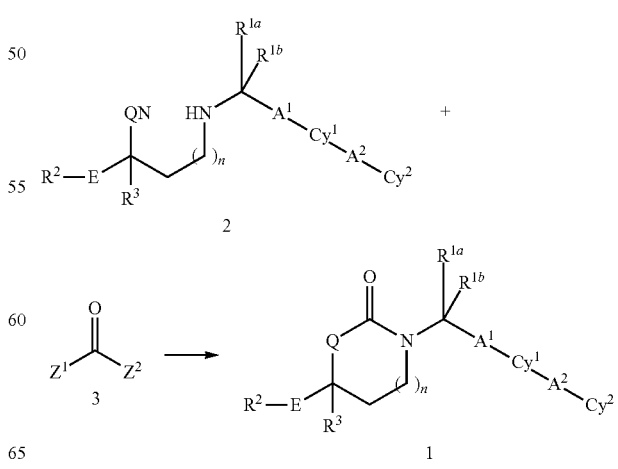

Intermediates of Formula 2 can be prepared by reduction of amides of Formula 4 using a hydride reagent such as borane in complex with e.g. tetrahydrofuran or dimethyl-sulfide or LiAlH$_4$ in an inert solvent such as tetrahydrofuran, ether, or 1,2-dimethoxyethane at 10° C. to 100° C.:

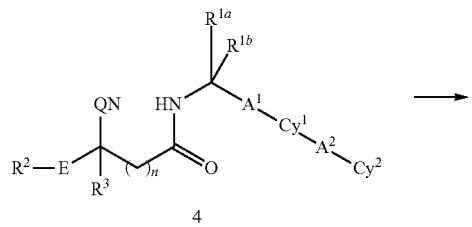

Intermediates of Formula 4 can be prepared by coupling of an hydroxyacid of Formula 5 (Q=O) or a protected aminoacid of Formula 5 (Q=NR$^5$) with an amine of Formula 6 using standard peptide coupling reagents such as N-(3-dimethylaminopropyl)-N'-ethylcarbodiimide or 2-(1H-benzotriazol-1-yl)-1,1,3,3-tetramethyluronium tetrafluoroborate both optionally in the presence of 1-hydroxybenzotriazole or 2,4,6-tripropyl-1,3,5,2,4,6-trioxatriphosphorinane-2,4,6-trioxide combined with a base such as N,N-diisopropyl-ethylamine in an inert solvent such as N,N-Dimethylformamide or CH$_2$Cl$_2$ at 0 to 60° C.:

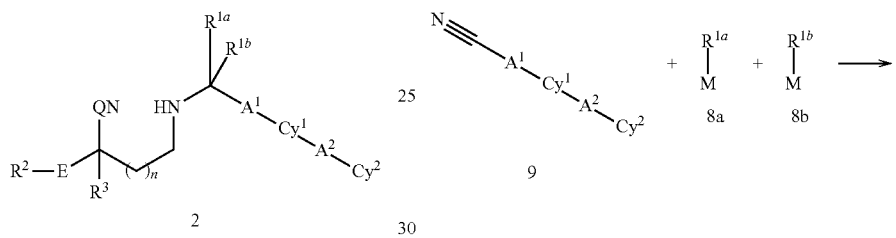

Amines of Formula 6 can be prepared by Ritter reaction of alcohols of Formula 7 with HCN:

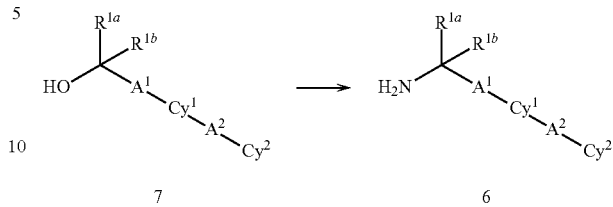

Amines of Formula 6 can also be prepared by addition of two nucleophiles of Formula 8a and 8b, which are added at once in case R$^{1a}$ equals R$^{1b}$ or successively in case they are different. M denotes preferably Li or MgHal or when R$^{1a}$ or R$^{1b}$ equals H M denotes preferably LiAlH$_3$ or Al(i-Bu)$_2$.

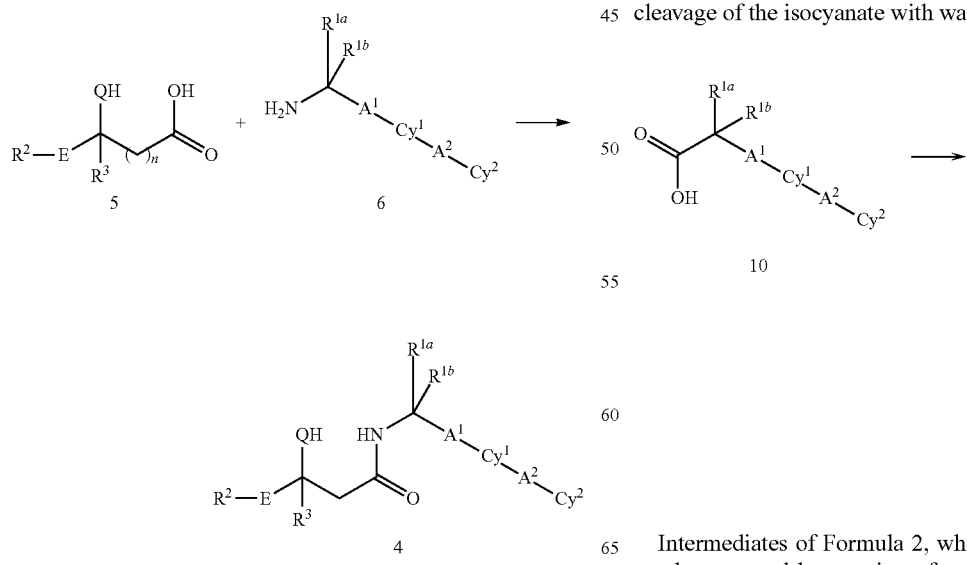

Another viable route to amines of Formula 6 is based on the Hofmann or Curtius rearrangement; starting from carboxylic acids of Formula 10 compounds 8 may be accessible by reaction with diphenylphosphoryl azide and subsequent cleavage of the isocyanate with water:

Intermediates of Formula 2, wherein Q=O and n=0 or 1, can be prepared by reaction of epoxides (n=0) or oxetanes (n=1) of Formula 11 with amines of Formula 6:

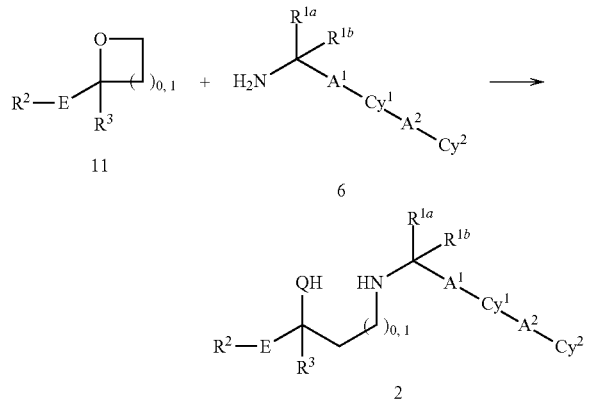

Intermediates of Formula 2, wherein Q denotes O or protected N, can also be prepared by reductive amination of aldehydes of Formula 12 with amines of Formula 6. Methods for the reductive amination of aldehydes are described in Baxter, E. W. and Reitz, A. B. "Organic Reactions" Volume 59, Ed. Overman, L. E., Wiley Interscience, 2002.

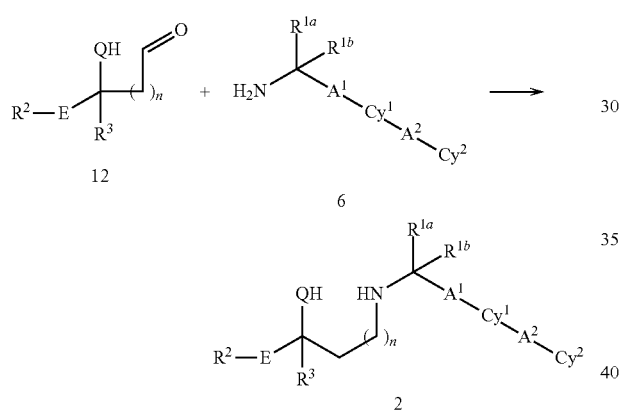

Amine intermediates of Formula 2, wherein Q=O or protected N, can be prepared by reaction of compounds of Formula 13, wherein LG is a leaving group and preferably denotes Cl, Br, I, or $OSO_2R^A$ ($R^A$=alkyl, haloalkyl or arylalkyl), with amines of Formula 6:

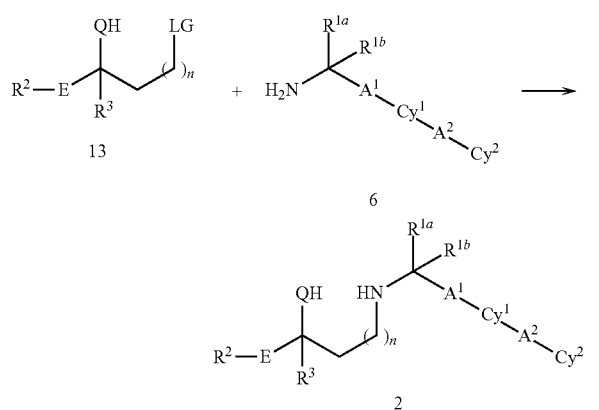

Intermediates of Formula 13, wherein Q=O or protected N and LG=Cl, Br, I, $OSO_2R^A$, can be prepared from alcohols of Formula 14; for LG=Cl, Br, I an electrophilic species of the respective halogen, e.g. N-halo-succinimide, tetrachloromethane, bromine, iodine, in combination with triphenylphosphine and for LG=$OSO_2R^A$ a sulfonyl chloride $R^ASO_2Cl$ combined with a base such as triethylamine or pyridine may be employed.

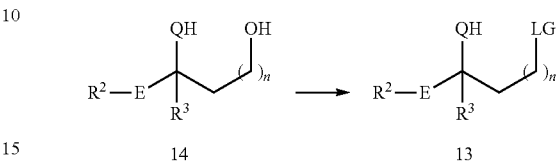

Intermediates of Formula 14, wherein n>0, can be prepared by hydroboration followed by oxidative cleavage of the C—B bond from alkenes of Formula 15:

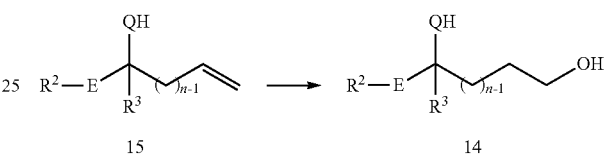

Alternatively, the same compounds of Formula 15, wherein n≥0, can be transformed into alcohols of Formula 14' by oxidative cleavage of the double bond, by e.g. ozonolysis, followed by reduction, with e.g. $NaBH_4$:

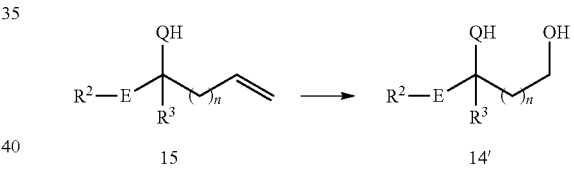

Halide intermediates of Formula 13, wherein LG=Cl, can be prepared by addition of an organometallic reagent of Formula 16, wherein M is preferably Li, MgCl, MgBr, MgI, ZnCl, ZnBr, ZnI, optionally in the presence of an additive such as $CeCl_3$, a zinc halide, or a Lewis acid such boron trifluoride etherate, with a ketone of Formula 17; the opposite constellation, i.e. $R^3$ is already part of compound 17 and $R^2$-E is introduced via an organometallic compound is analogously feasible:

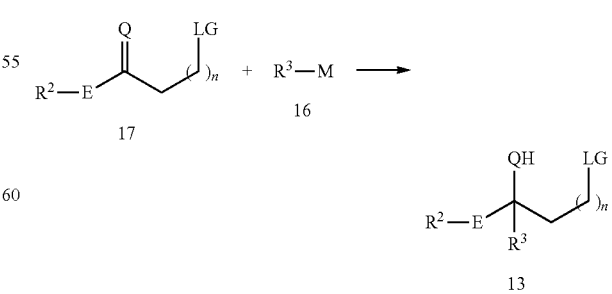

In a second process a compound of Formula I, wherein Q=O or $NR^S$, can be prepared by reaction of a carbamate of Formula 18, wherein $R^D$ is an alkyl or arylalkyl group such as methyl, t-butyl or benzyl, with a strong base such as NaH:

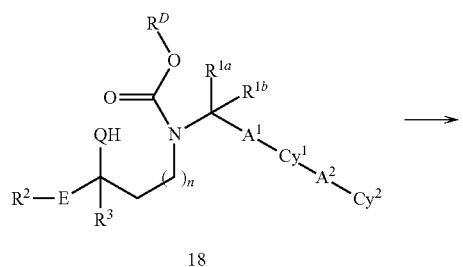

18

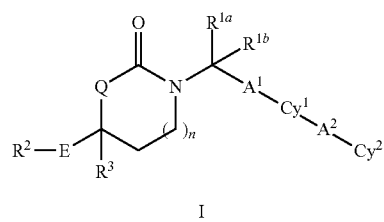

I

A carbamate of Formula 18 can be prepared by reaction of an amine of Formula 2, wherein Q=O or a protected N, with a chloroformate or an anhydride such as methyl or ethyl chloroformate or di-tert-butyl dicarbonate:

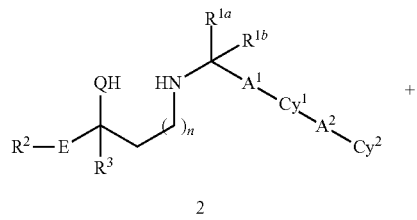

2

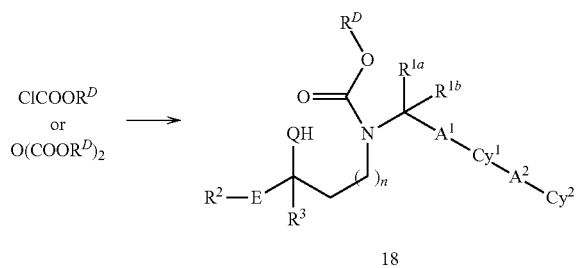

18

In a third process compounds of formula I can be prepared by reaction of a keto or iminocarbamate of formula 19, wherein Q is O or a protected N and $R^D$ is alkyl or arylalkyl such as methyl, t-butyl or benzyl, with an organometallic reagent of formula 20, wherein M encompasses but is not limited to ZnCl, ZnBr, ZnI, MgCl, MgBr, MgI, and Li:

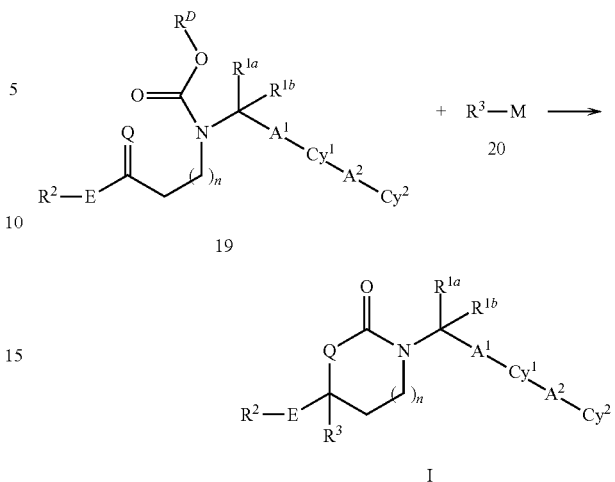

I

In specific examples organometallic reagent 20 is allylmagnesium bromide, allylzinc bromide, (2-methylallyl)magnesium chloride or (2-methoxy-2-oxoethyl)zinc bromide. In certain cases it may be advantageous to add $CeCl_3$ to the reaction mixture. The roles of $R^3$ and $R^2$-E can be reversed, i.e. $R^3$ is part of compound 19 and $R^2$-E is introduced via organometallic compound 20. Depending on the ease of accessability of intermediates 19 and 20 the former or latter proceeding may be favored (in the following potential syntheses of intermediate 19 only are delineated that, however, may be as well employed for the synthesis of the corresponding intermediate 19 incorporating $R^3$ instead of $R^2$).

Carbamates of formula 19 can be prepared by reaction of amines of formula 21, wherein Q is O or a protected N, with compounds of formula 3', wherein $R^E$ is a leaving group such as chlorine, succinyloxy, imidazolyl, or t-butoxycarboxy:

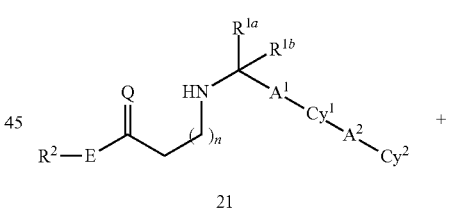

21

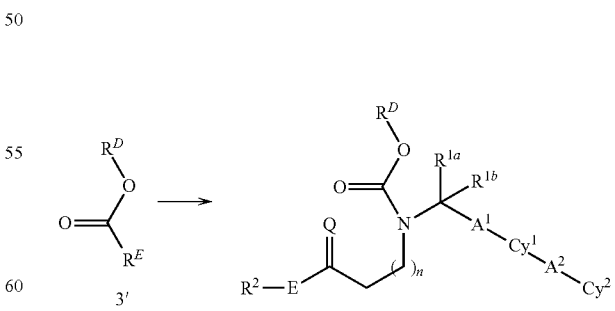

Amines of formula 21, wherein Q is O or a protected N and n equals 1, can be prepared by reaction of α,β-unsaturated ketones or imines of formula 22 with amines of formula 6:

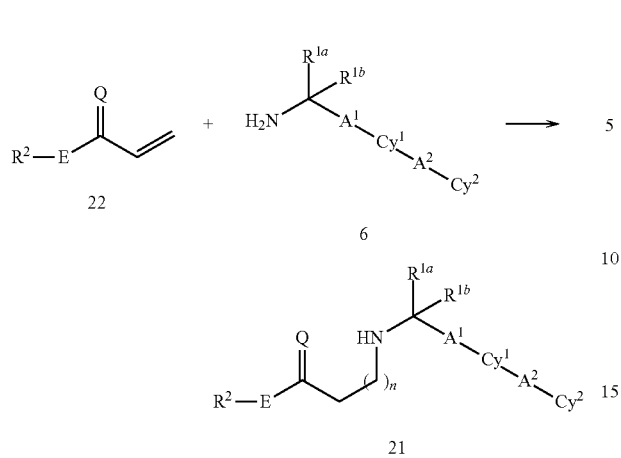

Alternatively, aminoketones or imines of formula 21, wherein Q is O or a protected N, can be prepared by reaction of ketones or imines of formula 23, wherein LG denotes a leaving group such as chlorine, bromine, iodine, methylsulfonyloxy, 4-tolylsulfonyloxy, or trifluoromethylsulfonyloxy, with amines of formula 6:

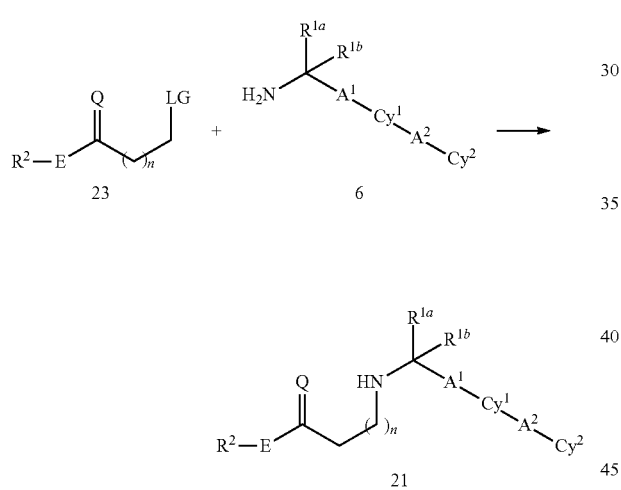

Ketones of formula 23, wherein Q is O, can in turn be prepared from α,β-unsaturated ketones of formula 22 by the formal addition of the corresponding LG-H such as HCl, HBr, HI, HOalkyl and HN(alkyl)$_2$.

Diamine intermediates of Formula 2' can be prepared by addition of organometallic reagents of Formula 20 to t-butylsulfinylimines of Formula 24:

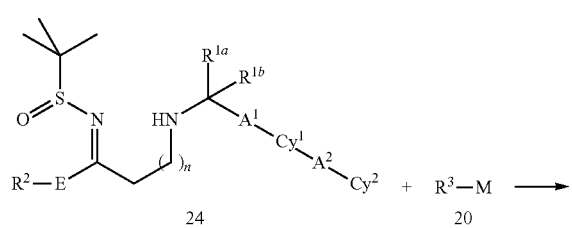

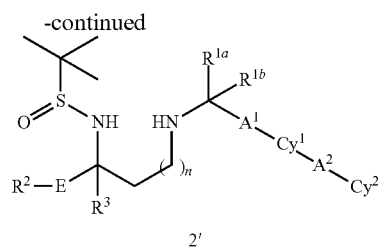

t-Butylsulfinylimines of Formula 24 can be prepared from aminoketones of Formula 21 by reaction with t-butylsulfinamide:

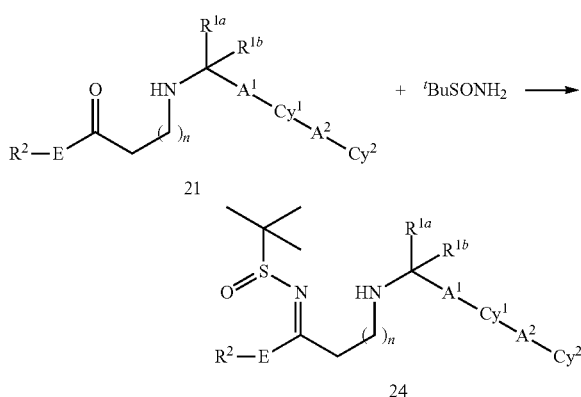

In the two transformations above it may be advantageous to protect the amino N in compounds 21 and 24 before conducting the respective reactions.

In a fourth process a compound of Formula I, wherein Q=O or NR$^5$, can be prepared by reaction of a compound of Formula 13 with an isocyanate of Formula 25 in the presence of a base:

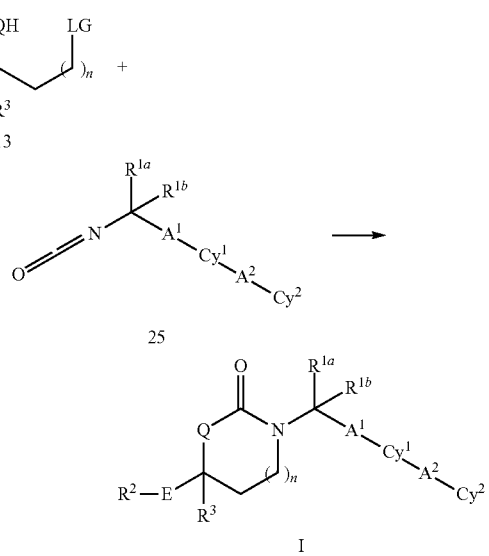

Isocyanates of Formula 25 can be prepared from amines of Formula 6 by treatment with phosgene, diphosgene, or triphosgene.

In a fifth process a compound of Formula I' can be prepared from a compound of Formula 26, wherein $R^D$ is a lower alkyl group such as methyl or ethyl and LG is a leaving group such as chloride, bromide, alkanesulfonate, arylsulfonate or haloalkanesulfonate, and an amine of Formula 6:

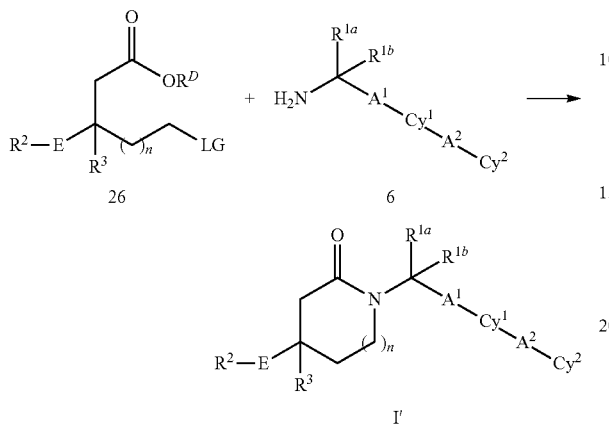

Intermediates of Formula 26, wherein E is a bond, $R^2$ is an aryl or heteroaryl group, LG is chloro and $R^3$ is allyl, can be prepared from alcohols of Formula 27 by treatment with allyltrimethylsilane in the presence of $TiCl_4$.

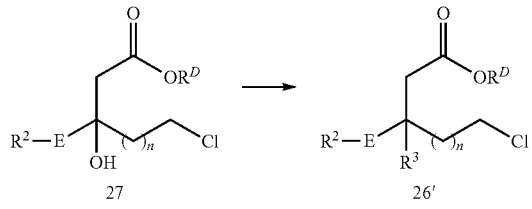

Alcohols of Formula 27 can be prepared by a Reformatsky reaction of zinc compounds of Formula 29 with chloroketones of Formula 28.

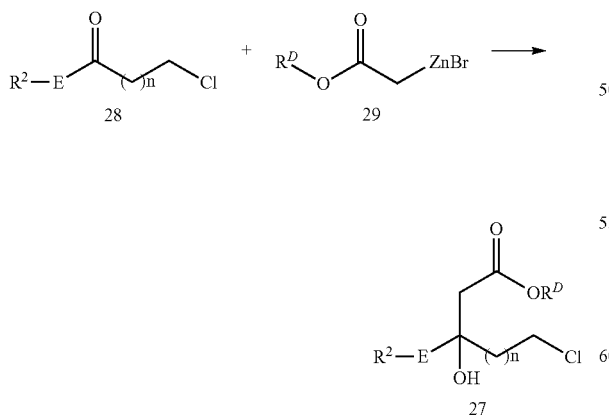

In a sixth process a compound of Formula I, wherein Q is $CH_2$ and $R^3$ is $CH_2CH_2OH$, can be prepared from an aminolactone of Formula 30 by heating:

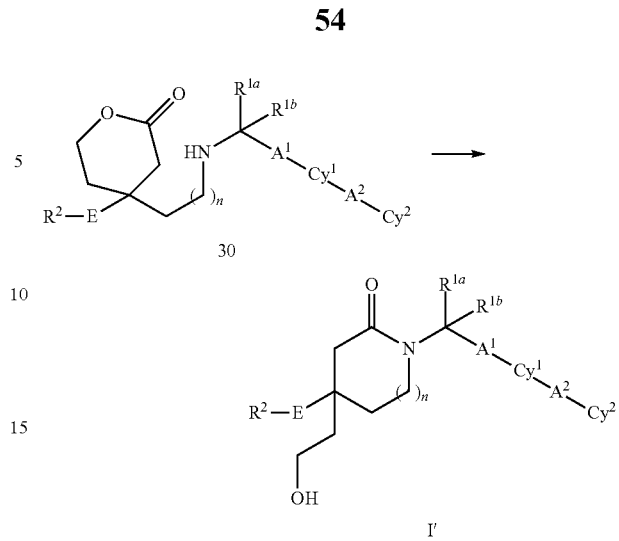

An aminolactone of Formula 30 can be prepared by reductive amination of an aldehyde of Formula 31 with an amine of Formula 6 using, for example, hydride reducing agents such as $Na(NC)BH_3$ or $NaB(OCOCH_3)_3H$ in the presence of acetic acid.

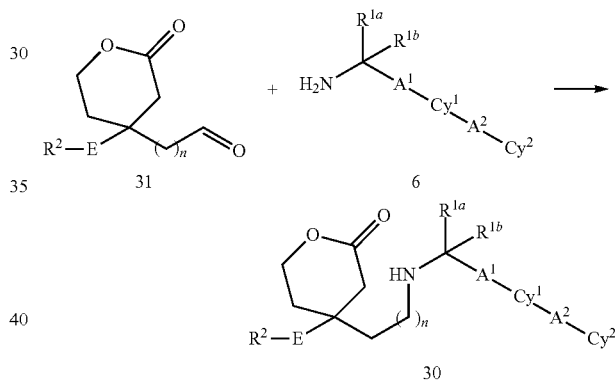

An aldehyde of Formula 31 can be prepared from an alkene of Formula 32 by ozonolysis followed by mild reductive work-up with e.g. dimethyl sulfide or triphenylphosphine or by hydroboration followed by oxidation.

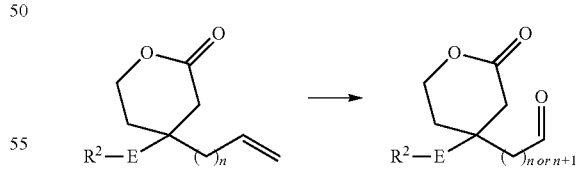

Allyl lactones of Formula 32 can be prepared by heating chloroesters of Formula 34 optionally in the presence of an additive such as a silver salt. Chloroesters of Formula 34 can in turn be prepared from hydroxyesters of Formula 33 by treatment with allylsilane in the presence of $TiCl_4$. Hydroxyesters of Formula 33 are available by a Reformatsky reaction of zinc compounds of Formula 29 and β-chloroketones of Formula 28'.

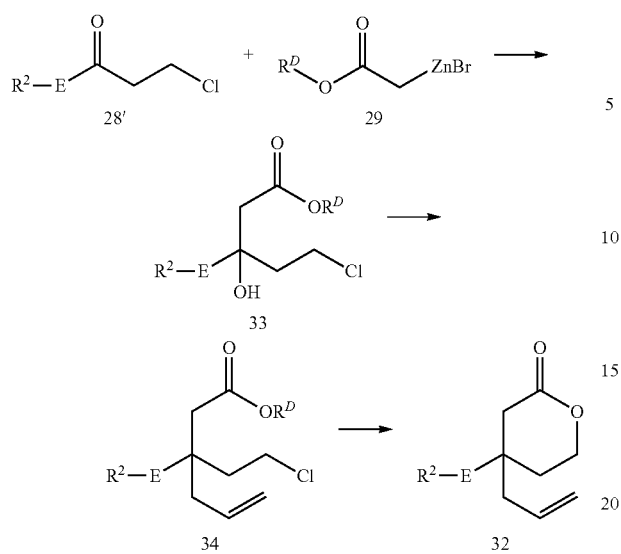

In a seventh process, a compound of Formula I, wherein $A^2$ is a bond and $Cy^1$ and $Cy^2$ are both independently selected to be aryl or heteroaryl, can be prepared from compounds of general Formula I', that are in turn obtained via the same synthetic routes which are described for compounds of formula I, and $Cy^2$-M, wherein LG is a leaving group such as iodine, bromine, chlorine or trifluoromethylsulfonyloxy and M a metal or pseudo-metal containing residue such as MgCl, MgBr, MgI, $B(OH)_2$, $BF_3K$, $B(OCH_2CH_2O)$, ZnCl, ZnBr, ZnI, $SnMe_3$, or $SnBu_3$.

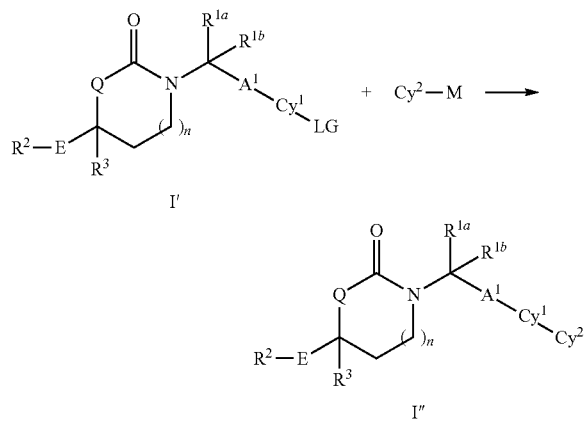

This transformation is preferably conducted with boron substituted $Cy^2$ as a Suzuki-Miyaura coupling reaction as described, for instance, in Example 111 of U.S. Provisional Patent Application No. 60/962,058, filed Jul. 26, 2007. The reactivity pattern of the two coupling partners may also be reversed, i.e. $Cy^1$ is the nucleophilic component bearing the boron (or other metal or pseudo-metal) residue and $Cy^2$ is the electrophilic partner bearing the halogen or pseudo-halogen group delivering the same coupling product of Formula I" under identical conditions. Alternatively, $Cy^1$ with a leaving group can also be combined with $Cy^2$-M, wherein M denotes H, by a transition metal, preferably palladium or copper catalyzed coupling reaction. Reactions of this type are particularly suited for heteroaromatic $Cy^2$-H as detailed in e.g. *Chem Sus Chem* 2008, 1, 404-407, *Eur. J. Inorg. Chem.* 2008, 2550-59, *J. Am. Chem. Soc.* 2008, 130, 15185-92, and references quoted therein.

In an eighth process, a compound of Formula I, wherein $A^1$ is ethynyl, can be prepared by Sonogashira coupling of a compound of Formula I''' with a compound of Formula 35, wherein LG is a leaving group such as iodine, bromine, chlorine or trifluoromethylsulfonyloxy:

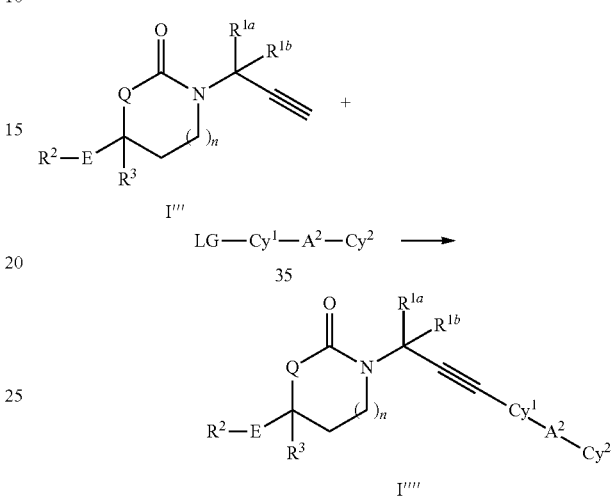

In a ninth process a compound of Formula I can be prepared from another compound of Formula I. For example:

(1) a compound of Formula I wherein $R^{1a}$, $R^{1b}$ or $R^3$ is hydroxymethyl($C_1$-$C_5$)alkyl can be oxidized to a compound of Formula I wherein $R^{1a}$, $R^{1b}$ or $R^3$ is carboxy($C_1$-$C_5$)alkyl using e.g. Jones reagent.

(2) a compound of Formula I wherein $R^{1a}$, $R^{1b}$ or $R^3$ is carboxy($C_1$-$C_6$)alkyl can be coupled with ammonia, a ($C_1$-$C_6$)alkylamine or a di-($C_1$-$C_6$)alkyl-amine using a standard peptide coupling reagent such as N-(3-dimethylaminopropyl)-N'-ethylcarbodiimide to afford a compound of Formula I wherein $R^{1a}$, $R^{1b}$ or $R^3$ is $H_2NC(=O)(C_1$-$C_6)$alkyl, $\{(C_1$-$C_6)$alkylNHC$(=O)\}(C_1$-$C_6)$alkyl or $\{[(C_1$-$C_6)$alkyl$]_2$NC$(=O)\}(C_1$-$C_6)$alkyl.

(3) a compound of Formula I wherein $R^{1a}$, $R^{1b}$ or $R^3$ is hydroxy($C_1$-$C_6$)alkyl can be converted to its methanesulfonate or trifluoromethanesulfonate, treated with sodium azide and reduced to give a compound of Formula I, wherein $R^{1a}$, $R^{1b}$ or $R^3$ is amino($C_1$-$C_6$)alkyl.

(4) a compound of Formula I wherein $R^{1a}$, $R^{1b}$ or $R^3$ is amino($C_1$-$C_6$)alkyl can be reacted with acetic anhydride or acetyl chloride to give a compound of Formula I wherein $R^{1a}$, $R^{1b}$ or $R^3$ is {acetylamino}($C_1$-$C_6$)alkyl.

(5) a compound of Formula I wherein $R^{1a}$, $R^{1b}$ or $R^3$ is amino($C_1$-$C_6$)alkyl can be reacted with methanesulfonyl chloride to give a compound of Formula I wherein $R^{1a}$, or $R^3$ is {methanesulfonylamino}($C_1$-$C_6$)alkyl.

(6) a compound of Formula I, wherein $R^{1a}$ or $R^{1b}$ is ($C_2$-$C_6$)alkenyl is hydroborated and subsequently oxidized to afford a compound of Formula I wherein $R^{1a}$ or $R^{1b}$ is hydroxy($C_2$-$C_6$)alkyl.

(7) a compound of Formula I, wherein $R^3$ is ($C_2$-$C_6$)alkenyl, is hydroborated and subsequently oxidized to afford a compound of Formula I wherein $R^3$ is hydroxy($C_2$-$C_6$)alkyl.

(8) a compound of Formula I, wherein $R^{1a}$ or $R^{1b}$ is ($C_2$-$C_6$)alkenyl, can be reacted with osmium tetroxide and N-methylmorpholine-N-oxide to afford a compound of Formula I wherein $R^1$ is vicinal dihydroxy($C_2$-$C_6$)alkyl.

(9) a compound of Formula I, wherein $R^3$ is ($C_2$-$C_6$)alkenyl, can be reacted with osmium tetroxide and N-methylmorpholine-N-oxide to afford a vicinal diol compound of Formula I wherein $R^3$ is vicinal dihydroxy($C_2$-$C_6$)alkyl.

(10) a compound of Formula I, wherein $R^{1a}$ or $R^{1b}$ is ($C_2$-$C_6$)alkenyl, can be reacted with ozone followed by $NaBH_4$ reduction to give a compound of Formula I wherein $R^{1a}$ or $R^{1b}$ is hydroxy($C_1$-$C_5$)alkyl.

(11) a compound of Formula I, wherein $R^3$ is ($C_2$-$C_6$)alkenyl, can be reacted with ozone followed by $NaBH_4$ reduction to give a compound of Formula I wherein $R^3$ is hydroxy($C_1$-$C_5$)alkyl.

(12) a compound of Formula I wherein $R^{1a}$, $R^{1b}$ or $R^3$ is amino($C_1$-$C_6$)alkyl can be reacted with an ($C_1$-$C_6$)alkyl isocyanate to give a compound of Formula I wherein $R^{1a}$, $R^{1b}$ or $R^3$ is ($C_1$-$C_6$)alkylaminocarbonylamino($C_1$-$C_6$)alkyl.

(13) a compound of Formula I wherein $R^{1a}$, $R^{1b}$ or $R^3$ is amino($C_1$-$C_6$)alkyl can be reacted with an ($C_1$-$C_6$)alkyl chloroformate to give a compound of Formula I wherein $R^{1a}$, $R^{1b}$ or $R^3$ is ($C_1$-$C_6$)alkoxycarbonylamino($C_1$-$C_6$)alkyl.

(14) a compound of Formula I wherein $R^{1a}$, $R^{1b}$ or $R^3$ is amino($C_1$-$C_6$)alkyl can be reacted with chlorosulfonyl isocyanate or sulfamide to give a compound of Formula I wherein $R^{1a}$, $R^{1b}$ or $R^3$ is aminosulfonylamino($C_1$-$C_6$)alkyl.

(15) a compound of Formula I wherein $R^{1a}$, $R^{1b}$ or $R^3$ is amino($C_1$-$C_6$)alkyl can be reacted with a ($C_1$-$C_6$)alkylsulfamoyl chloride to give a compound of Formula I wherein $R^{1a}$, $R^{1b}$ or $R^3$ is ($C_1$-$C_6$)alkylaminosulfonylamino($C_1$-$C_6$)alkyl.

(16) a compound of Formula I wherein $R^{1a}$, $R^{1b}$ or $R^3$ is hydroxy($C_1$-$C_6$)alkyl can be reacted with chlorosulfonyl isocyanate to give a compound of Formula I wherein $R^{1a}$, $R^{1b}$ or $R^3$ is aminosulfonyloxy($C_1$-$C_6$)alkyl.

(17) a compound of Formula I wherein $R^{1a}$, $R^{1b}$ or $R^3$ is hydroxy($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^{1a}$, $R^{1b}$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$)alkyl.

(18) a compound of Formula I wherein $R^{1a}$, $R^{1b}$ or $R^3$ is hydroxy($C_1$-$C_6$)alkyl can be reacted with $POCl_3$ to give a compound of Formula I wherein $R^{1a}$, $R^{1b}$ or $R^3$ is $(HO)_2P(=O)O(C_1$-$C_6$)alkyl.

(19) a compound of Formula I, wherein $R^3$ is allyl or homoallyl can be reacted with oxygen in the presence of $PdCl_2$ and CuCl to afford a compound of Formula I, wherein $R^3$ is 2-oxopropyl or 3-oxobutyl respectively.

(20) a compound of Formula I, wherein $R^3$ is 2-oxopropyl or 3-oxobutyl can be reacted with MeMgX, wherein X is Cl, Br or I, to give a compound of Formula I, wherein $R^3$ is 2-hydroxy-2-methylpropyl or 3-hydroxy-3-methylpropyl, respectively.

(21) a compound of Formula I, wherein $R^3$ is —$CH_2CO_2Me$ can be treated with MeMgX, wherein X is Cl, Br or I, to give a compound of Formula I, wherein $R^3$ is 2-hydroxy-2-methylpropyl.

(22) a compound of Formula I, wherein $R^3$ is allyl or —$CH_2C(Me)=CH_2$ can be hydrocyanated with 4-tolylsulfonyl cyanide in the presence of triphenylsilane and a cobalt catalyst to afford compounds of Formula I, wherein $R^3$ is —$CH_2CH(CN)Me$ or —$CH_2CMe_2CN$ respectively.

(23) a compound of Formula I wherein $R^3$ is $CH_2C(Me)_2CN$, can be treated with acetamide in the presence of $PdCl_2$ to give a compound of Formula I, wherein $R^3$ is $CH_2CMe_2CONH_2$.

(24) a compound of Formula I, wherein $R^3$ is —$CH_2C(Me)=CH_2$ can be treated with 3-chloroperoxybenzoic acid followed by lithium triethylborohydride to afford a compound of Formula I, wherein $R^3$ is 2-hydroxy-2-methylpropyl.

| LC-MS METHODS Method 1: Agilent 1200 | |
|---|---|
| Column | Waters Xbridge C18 30 × 4.6 mm 2.5 μm |
| Mobile Phase | A: water + 0.1% $F_3CCO_2H$<br>B: acetonitrile |

| TIME (min) | A% | B% |
|---|---|---|
| 0 | 90 | 10 |
| 0.15 | 90 | 10 |
| 3.15 | 10 | 90 |
| 4.50 | 10 | 90 |
| 4.75 | 20 | 10 |
| 5.00 | 20 | 10 |

| | |
|---|---|
| Flow Rate | 1.2 mL/min |
| Wavelength | UV 220, 230, or 254 nm |

PREPARATION 1

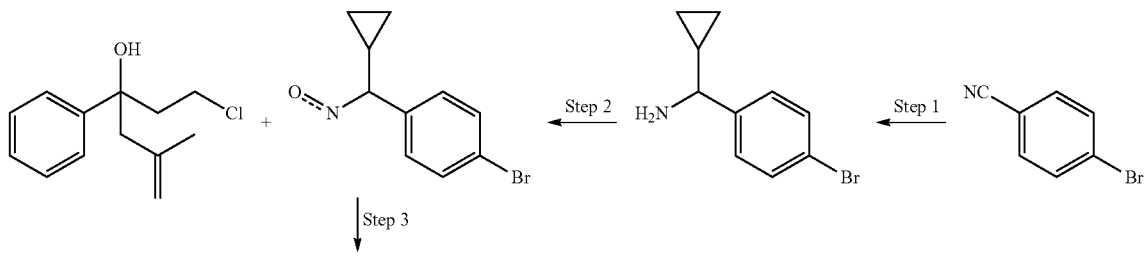

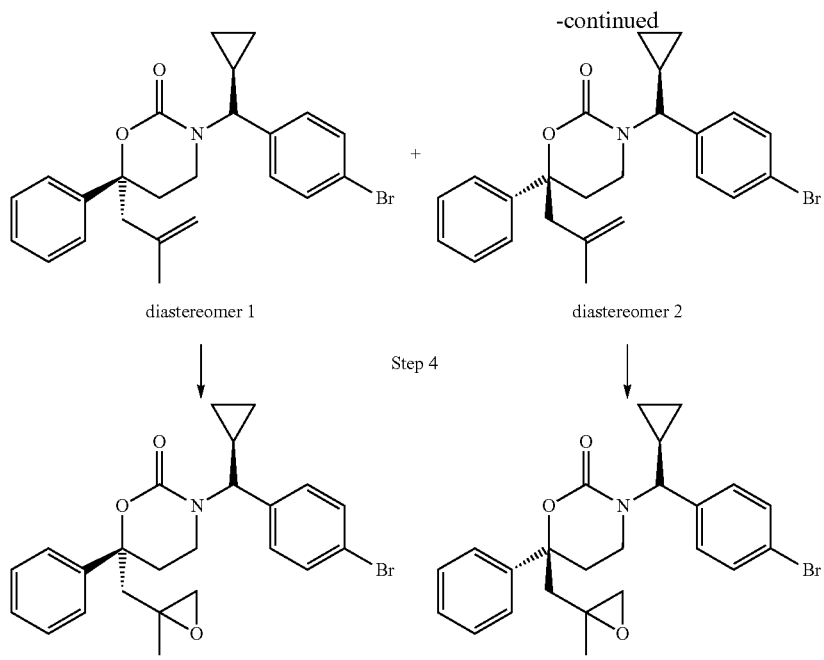

diastereomer 1 + diastereomer 2

Step 4

Step 1 (4-Bromo-phenyl)-cyclopropyl-methylamine

A solution of 4-bromo-benzonitrile (6.30 g) in tetrahydrofuran (50 mL) was added over a period of 20 min to a 0.5 M solution of cyclopropylmagnesium bromide in tetrahydrofuran (200 mL) chilled in an ice bath. After stirring the resulting solution with cooling for 5.5 h, methanol (100 mL) was added over a period of 20 min. Then sodium borohydride (2.65 g) was added portionwise and the resulting mixture was warmed to room temperature overnight. Aqueous saturated $NaHCO_3$ solution was added and then the pH value of the mixture was adjusted to 8-9 using 1 M hydrochloric acid. The resulting mixture was extracted with dichloromethane and the combined extracts were washed with water and dried ($MgSO_4$). The solvent was evaporated to leave an oil that was dissolved in dichloromethane. The resulting solution was extracted with 1 M hydrochloric acid and the combined aqueous extracts were basified (pH value ca. 8-9) with 4 M aqueous NaOH solution. The aqueous solution was extracted with dichloromethane and the combined organic extracts were washed with water and dried ($MgSO_4$). The solvent was evaporated to afford the title compound as an oil. Yield: 5.56 g (72% of theory); Mass spectrum ($ESI^+$): m/z=209/211 (Br) $[M+H-NH_3]^+$.

Step 2 1-Bromo-4-(cyclopropyl-isocyanato-methyl)-benzene

Triphosgene (1.31 g) was added at once to a vigorously stirred mixture of $NaHCO_3$ (2.14 g) in water (50 mL) and (4-bromo-phenyl)-cyclopropyl-methylamine (2.50 g) in dichloromethane (50 mL) chilled in an ice bath. The cooling bath was removed and the mixture was stirred at room temperature for another 30 min. Then the organic phase was separated and dried ($MgSO_4$) and the solvent was evaporated to afford the isocyanate as an oil that was directly submitted to the next reaction step. Yield: 2.88 g (quantitative); Mass spectrum ($ESI^-$): m/z=250/252 (Br) $[M-H]^-$.

Step 3 3-[(4-Bromo-phenyl)-cyclopropyl-methyl]-6-(2-methyl-allyl)-6-phenyl-[1,3]oxazinan-2-one Lithium hexamethyldisilazide (1 mol/L in tetrahydrofuran, 12.6 mL) was added dropwise (at such a rate that the solution temperature maintains below 25° C.) to a solution of 1-chloro-5-methyl-3-phenyl-hex-5-en-3-ol (2.57 g) and 1-bromo-4-(cyclopropyl-isocyanato-methyl)-benzene (2.88 g) in tetrahydrofuran (75 mL) chilled in an ice bath. The solution was stirred in the cooling bath for another 30 min and at room temperature for another 60 min. Then acetic acid (1.6 mL) in water (40 mL) was added slowly to the reaction mixture. The resulting mixture was concentrated under reduced pressure and the residue was taken up in tert-butyl methyl ether. The resulting solution was washed with water, dried ($MgSO_4$), and concentrated. The residue was submitted to chromatography on silica gel (cyclohexane/ethyl acetate 90:10→40:60) to afford diastereomer 1 as a white solid and diastereomer 2 as a resin-like solid.

Diastereomer 1: Yield: 1.32 g (26% of theory); Mass spectrum ($ESI^+$): m/z=440/442 (Br) $[M+H]^+$; $^1H$ NMR (400 MHz, DMSO-$d_6$) −0.13-0.66 (m, 1H), ca. −0.02-0.07 (m, 1H), 0.33-0.42 (m, 1H), 0.60-0.68 (m, 1H), 1.03-1.14 (m, 1H), 1.56 (s, 3H), 2.05-2.15 (m, 1H), 2.45-ca. 2.48 (m, 1H), 2.57 (d, J=14.7 Hz, 1H, A part of an AB-signal), 2.61 (d, J=14.7 Hz, 1H, B part of an AB-signal), 2.79-2.91 (m, 2H), 4.35 (d, J=10.4 Hz, 1H), 4.60 ($m_c$, 1H), 4.76 ($m_c$, 1H), 7.27-7.44 (m, 7H), 7.55 (dm, J=8.5 Hz, 2H).

Diastereomer 2: Yield: 1.49 g (30% of theory); Mass spectrum ($ESI^+$): m/z=440/442 (Br) $[M+H]^+$; $^1H$ NMR (400 MHz, DMSO-$d_6$) 0.32-44 (m, 2 H), 0.52-0.60 (m, 1H), 0.71-0.79 (m, 1H), 1.34-1.44 (m, 1H), 1.55 (s, 3H), 2.17-2.27 (m, 1H), 2.37-ca. 2.50 (m, 2H), 2.58 (s, 3H), 4.38 (d, J=10.3 Hz, 1H), 4.60 ($m_c$, 1H), 4.78 ($m_c$, 1H), 6.88 (d, J=8.3 Hz, 2H), 7.28 (dm, J=8.3 Hz, 2H), 7.30-7.41 (m, 5H).

The stereochemical assignments of the diastereomers are based on the comparison of the $^1H$ NMR data with the data of the known analogs 3-[(S)-1-(4-bromo-phenyl)-ethyl]-(S)-6-

(2-methyl-allyl)-6-phenyl-[1,3]oxazinan-2-one and 3-[(S)-1-(4-bromo-phenyl)-ethyl]-(R)-6-(2-methyl-allyl)-6-phenyl-[1,3]oxazinan-2-one.

Step 4 3-[(4-Bromo-phenyl)-cyclopropyl-methyl]-6-(2-methyl-oxiranylmethyl)-6-phenyl-[1,3]oxazinan-2-one (racemic mixture of the diastereomer drawn)

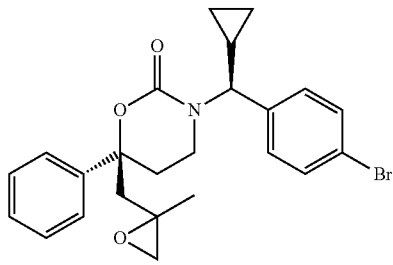

3-[(4-Bromo-phenyl)-cyclopropyl-methyl]-6-(2-methyl-allyl)-6-phenyl-[1,3]oxazinan-2-one (diastereomer 2 from Step 3; 1.60 g) dissolved in dichloromethane (15 mL) was added to a solution of 3-chloroperoxybenzoic acid (77%, 0.94 g) in dichloromethane (15 mL) cooled to 5° C. The solution was stirred at room temperature for 3 h, before another portion of 3-chloroperoxybenzoic acid (77%, 0.13 g) was added. After stirring the solution at room temperature for another 1.5 h, aqueous 10% Na$_2$S$_2$O$_3$ solution (10 mL) and aqueous saturated NaHCO$_3$ solution (10 mL) were added and the resulting mixture was stirred for further 30 min. Dichloromethane (20 mL) was added and the organic phase was separated and washed with a 1:1 mixture of aqueous 10% Na$_2$S$_2$O$_3$ solution and aqueous saturated NaHCO$_3$ solution. Then the organic phase was washed with water, dried (MgSO$_4$), and concentrated to furnish the title compound. Yield: 1.86 g (ca. 85-90% pure, quantitative); LC-MS (Method 1): $t_R$=4.00 min; Mass spectrum (ESI$^+$): m/z=456/458 (Br) [M+H]$^+$.

3-[(4-Bromo-phenyl)-cyclopropyl-methyl]-6-(2-methyl-oxiranylmethyl)-6-phenyl-[1,3]oxazinan-2-one (racemic mixture of the diastereomer drawn)

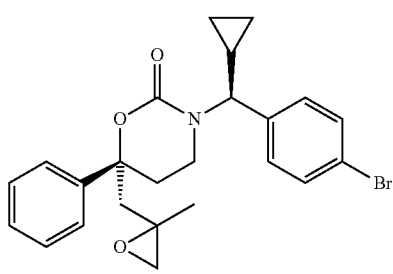

The title compound was prepared from 3-[(4-bromo-phenyl)-cyclopropyl-methyl]-6-(2-methyl-allyl)-6-phenyl-[1,3]oxazinan-2-one (diastereomer 1 from Step 3) following a procedure analogous to that described for the diastereomer above. LC-MS (Method 1): $t_R$=4.02 min; Mass spectrum (ESI$^+$): m/z=456/458 (Br) [M+H]$^+$.

EXAMPLE 1

3-[(4-Bromo-phenyl)-cyclopropyl-methyl]-6-(2-hydroxy-2-methyl-propyl)-6-phenyl-[1,3]oxazinan-2-one (racemic mixture of the diastereomer drawn)

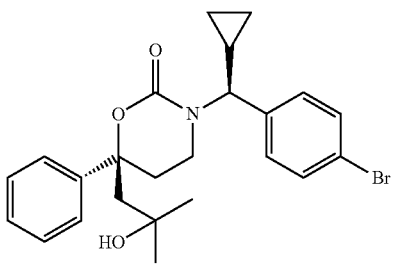

Lithium triethylborohydride (1 mol/L in tetrahydrofuran, 4.9 mL) was added to an ice-cold solution of 3-[(4-bromo-phenyl)-cyclopropyl-methyl]-6-(2-methyl-oxiranylmethyl)-6-phenyl-[1,3]oxazinan-2-one (compound processed from diastereomer 2 obtained in Step 3; 1.86 g, ca. 85-90% pure) in tetrahydrofuran (15 mL) at such a rate that the solution temperature remained below 10° C. The resulting solution was stirred in the cooling bath for one more hour and at room temperature for another 3 h. Then, the solution was cooled in an ice bath and the reaction was quenched by the careful addition of water (7 mL). After the addition of hydrochloric acid and ethyl acetate, the organic phase was separated, washed with brine, and dried (MgSO$_4$). The solvent was evaporated to afford the title compound. Yield: 1.45 g (88% of theory); Mass spectrum (ESI$^+$): m/z=458/460 (Br) [M+H]$^+$.

EXAMPLE 2

3-[(4-Bromo-phenyl)-cyclopropyl-methyl]-6-(2-hydroxy-2-methyl-propyl)-6-phenyl-[1,3]oxazinan-2-one (racemic mixture of the diastereomer drawn)

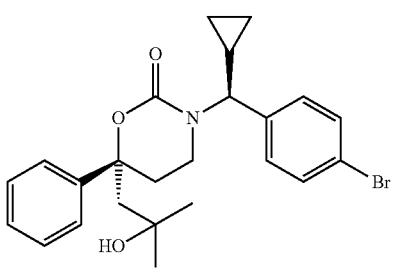

The title compound was prepared from 3-[(4-bromo-phenyl)-cyclopropyl-methyl]-6-(2-methyl-oxiranylmethyl)-6-phenyl-[1,3]oxazinan-2-one (compound processed from diastereomer 1 obtained in Step 3) following a procedure analogous to that described in Example 1. LC-MS (Method 1): $t_R$=4.01 min; Mass spectrum (ESI$^+$): m/z=458/460 (Br) [M+H]$^+$.

EXAMPLE 3

3-{Cyclopropyl-[4-(1-methyl-2-oxo-1,2-dihydro-pyridin-4-yl)-phenyl]-methyl}-6-(2-hydroxy-2-methyl-propyl)-6-phenyl-[1,3]oxazinan-2-one (racemic mixture of the diastereomer drawn)

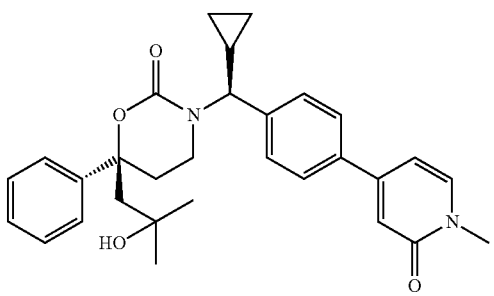

The racemic mixture was also resolved into its enantiomers,

EXAMPLE 3a (=EXAMPLE 7)

3-{(S)-cyclopropyl-[4-(1-methyl-2-oxo-1,2-dihydro-pyridin-4-yl)-phenyl]methyl}-(S)-6-(2-hydroxy-2-methyl-propyl)-6-phenyl-[1,3]oxazinan-2-one and

EXAMPLE 3b

3-{(R)-cyclopropyl-[4-(1-methyl-2-oxo-1,2-dihydro-pyridin-4-yl)-phenyl]methyl}-(R)-6-(2-hydroxy-2-methyl-propyl)-6-phenyl-[1,3]oxazinan-2-one, by chromatography on chiral phase [Daicel IA, 250 mm×4.6 mm, 4 mL/min, scCO$_2$/methanol (containing diethylamine)].

3-{Cyclopropyl-[4-(4,4,5,5-tetramethyl-[1,3,2]dioxaborolan-2-yl)-phenyl]methyl}-6-(2-hydroxy-2-methyl-propyl)-6-phenyl-[1,3]oxazinan-2-one (racemic mixture of the diastereomer drawn)

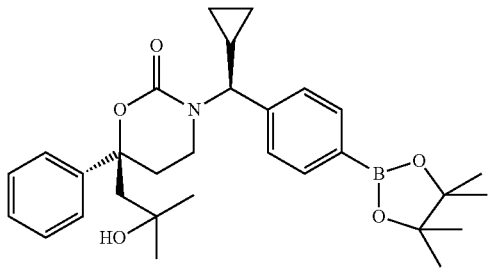

2 M aqueous Na$_2$CO$_3$ solution (0.69 mL) was added to a mixture of 4-bromo-1-methyl-1H-pyridin-2-one (0.14 g) and 3-{cyclopropyl-[4-(4,4,5,5-tetramethyl-[1,3,2]dioxaborolan-2-yl)-phenyl]methyl}-6-(2-hydroxy-2-methyl-propyl)-6-phenyl-[1,3]oxazinan-2-one (pure diastereomer; 0.35 g) in N,N-dimethylformamide (4 mL). The resulting mixture was sparged with argon for 10 min, before [1,1'-bis(diphenylphosphino)-ferrocene]dichloro-palladium(II) dichloromethane complex (57 mg) was added. The mixture was heated to 100° C. and stirred at this temperature for 4 h. After cooling the mixture to ambient temperature, water was added and the resulting mixture was extracted with ethyl acetate. The combined organic extracts were washed with water and brine and dried (MgSO$_4$). The solvent was evaporated and the residue was purified by HPLC on reversed phase (methanol/water/NH$_4$OH) to afford the title compound. Yield: 0.36 g (52% of theory); LC-MS (Method 1): $t_R$=3.31 min; Mass spectrum (ESI$^+$): m/z=487 [M+H]$^+$.

A flask charged with a stir bar, potassium acetate (1.23 g), bis(pinacolato)diboron (1.18 g), 3-[(4-bromo-phenyl)-cyclopropyl-methyl]-6-(2-hydroxy-2-methyl-propyl)-6-phenyl-[1,3]oxazinan-2-one (compound from Example 1; 1.45 g), and dimethyl sulfoxide (20 mL) was sparged with argon for 10 min. Then, [1,1'-bis(diphenylphosphino)ferrocene]dichloro-palladium(II) dichloromethane complex (0.29 g) was added and the mixture was heated to 90° C. and stirred at this temperature for 2.5 h. After cooling the mixture to ambient temperature, water and ethyl acetate were added and the resulting mixture was filtered over Celite. The aqueous phase of the filtrate was separated and extracted twice with ethyl acetate. The organic extracts and the organic phase of the filtrate were combined and washed with water and brine and dried (MgSO$_4$). The solvent was evaporated and the residue was purified by chromatography on silica gel (cyclohexane/ethyl acetate 1:1→1:4) to afford the title compound. Yield:

1.14 g (71% of theory); LC-MS (Method 1): $t_R$=2.91 min; Mass spectrum (ESI$^+$): m/z=506 [M+H]$^+$.

EXAMPLE 4

3-{Cyclopropyl-[4-(1-methyl-2-oxo-1,2-dihydro-pyridin-4-yl)-phenyl]-methyl}-6-(2-hydroxy-2-methyl-propyl)-6-phenyl-[1,3]oxazinan-2-one (racemic mixture of the diastereomer drawn)

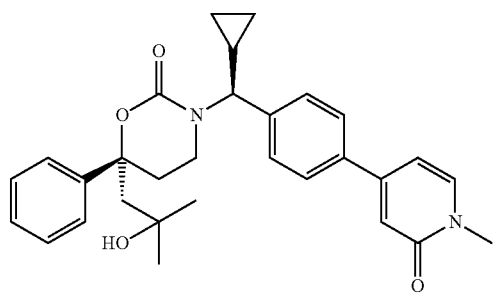

The title compound was prepared from 3-{cyclopropyl-[4-(4,4,5,5-tetramethyl-[1,3,2]dioxaborolan-2-yl)-phenyl]methyl}-6-(2-hydroxy-2-methyl-propyl)-6-phenyl-[1,3]oxazinan-2-one (for preparation see below) and 4-bromo-1-methyl-1H-pyridin-2-one following a procedure analogous to that described in Example 3. LC-MS (Method 1): $t_R$=3.57 min; Mass spectrum (ESI$^+$): m/z=487 [M+H]$^+$.

3-{Cyclopropyl-[4-(4,4,5,5-tetramethyl-[1,3,2]dioxaborolan-2-yl)-phenyl]methyl}-6-(2-hydroxy-2-methyl-propyl)-6-phenyl-[1,3]oxazinan-2-one (racemic mixture of the diastereomer drawn)

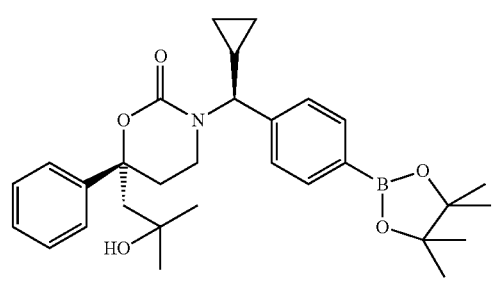

The title compound was prepared from 3-[(4-bromo-phenyl)-cyclopropyl-methyl]-6-(2-hydroxy-2-methyl-propyl)-6-phenyl-[1,3]oxazinan-2-one (compound from Example 2) following a procedure analogous to that described in Example 3. LC-MS (Method 1): $t_R$=2.91 min; Mass spectrum (ESI$^+$): m/z=506 [M+H]$^+$.

EXAMPLE 5

3-{Cyclopropyl-[4-(1-methyl-6-oxo-1,6-dihydro-pyridin-3-yl)-phenyl]-methyl}-6-(2-hydroxy-2-methyl-propyl)-6-phenyl-[1,3]oxazinan-2-one (racemic mixture of the diastereomer drawn)

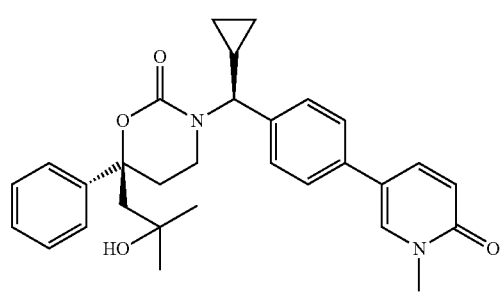

The title compound was prepared from 3-{cyclopropyl-[4-(4,4,5,5-tetramethyl-[1,3,2]dioxaborolan-2-yl)-phenyl]methyl}-6-(2-hydroxy-2-methyl-propyl)-6-phenyl-[1,3]oxazinan-2-one (for preparation see Example 3) and 5-bromo-1-methyl-1H-pyridin-2-one following a procedure analogous to that described in Example 3. LC-MS (Method 1): $t_R$=3.34 min; Mass spectrum (ESI$^+$): m/z=487 [M+H]$^+$.

EXAMPLE 6

3-[(S)-(4-Bromo-phenyl)-cyclopropyl-methyl]-(S)-6-(2-hydroxy-2-methyl-propyl)-6-phenyl-[1,3]oxazinan-2-one

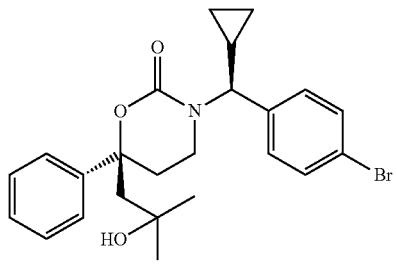

The title compound was prepared from 3-[(S)-(4-bromo-phenyl)-cyclopropyl-methyl]-(S)-6-(2-methyl-oxiranylmethyl)-6-phenyl-[1,3]oxazinan-2-one (prepared from (S)-(4-bromo-phenyl)-cyclopropyl-methylamine in analogy to Preparation 1) following a procedure analogous to that described in Example 1. LC-MS (Method 1): $t_R$=4.01 min; Mass spectrum (ESI$^+$): m/z=458/460 (Br) [M+H]$^+$.

EXAMPLE 7 (=EXAMPLE 3a)

3-{(S)-Cyclopropyl-[4-(1-methyl-2-oxo-1,2-dihydro-pyridin-4-yl)-phenyl]-methyl}-(S)-6-(2-hydroxy-2-methyl-propyl)-6-phenyl-[1,3]oxazinan-2-one

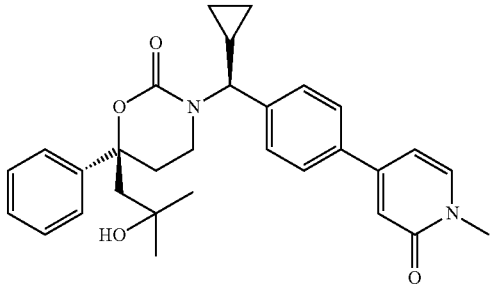

The title compound was prepared from 3-{(S)-cyclopropyl-[4-(4,4,5,5-tetramethyl-[1,3,2]dioxaborolan-2-yl)-phenyl]methyl}-(S)-6-(2-hydroxy-2-methyl-propyl)-6-phenyl-[1,3]oxazinan-2-one {prepared in analogy to the intermediate in Example 3 from 3-[(S)-(4-bromo-phenyl)-cyclopropyl-methyl]-(S)-6-(2-hydroxy-2-methyl-propyl)-6-phenyl-[1,3]oxazinan-2-one} and 4-bromo-1-methyl-1H-pyridin-2-one following a procedure analogous to that described in Example 3. LC-MS (Method 1): $t_R$=3.34 min; Mass spectrum (ESI$^+$): m/z=487 [M+H]$^+$.

EXAMPLE 8

3-{(S)-Cyclopropyl-[4-(6-methyl-pyridazin-3-yl)-phenyl]methyl}-(S)-6-(2-hydroxy-2-methyl-propyl)-6-phenyl-[1,3]oxazinan-2-one

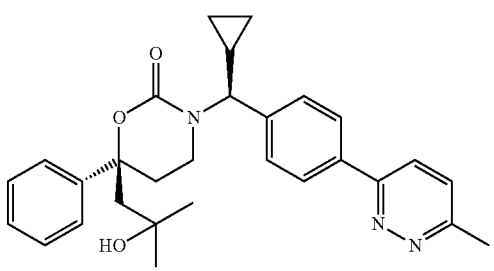

The title compound was prepared from 3-{(S)-cyclopropyl-[4-(4,4,5,5-tetramethyl-[1,3,2]dioxaborolan-2-yl)-phenyl]methyl}-(S)-6-(2-hydroxy-2-methyl-propyl)-6-phenyl-[1,3]oxazinan-2-one {prepared in analogy to the intermediate in Example 3 from 3-[(S)-(4-bromo-phenyl)-cyclopropyl-methyl]-(S)-6-(2-hydroxy-2-methyl-propyl)-6-phenyl-[1,3]oxazinan-2-one} and 3-chloro-6-methyl-pyridazine following a procedure analogous to that described in Example 3. LC-MS (Method 1): $t_R$=3.39 min; Mass spectrum (ESI$^+$): m/z=472 [M+H]$^+$.

EXAMPLE 9

3-{(S)-Cyclopropyl-[4-(1-cyclopropyl-2-oxo-1,2-dihydro-pyridin-4-yl)-phenyl]-methyl}-(S)-6-(2-hydroxy-2-methyl-propyl)-6-phenyl-[1,3]oxazinan-2-one

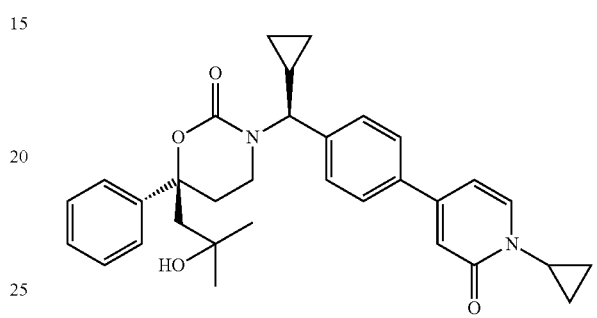

The title compound was prepared from 3-{(S)-cyclopropyl-[4-(4,4,5,5-tetramethyl-[1,3,2]dioxaborolan-2-yl)-phenyl]-methyl}-(S)-6-(2-hydroxy-2-methyl-propyl)-6-phenyl-[1,3]oxazinan-2-one {prepared in analogy to the intermediate in Example 3 from 3-[(S)-(4-bromo-phenyl)-cyclopropyl-methyl]-(S)-6-(2-hydroxy-2-methyl-propyl)-6-phenyl-[1,3]oxazinan-2-one} and 4-bromo-1-cyclopropyl-1H-pyridin-2-one following a procedure analogous to that described in Example 3. LC-MS (Method 1): $t_R$=3.49 min; Mass spectrum (ESI$^+$): m/z=513 [M+H]$^+$.

4-Bromo-1-cyclopropyl-1H-pyridin-2-one

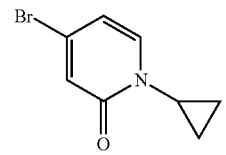 [SMILES: O=c1cc(Br)ccn1C1CC1]

A flask charged with a stir bar, 4-bromo-1H-pyridin-2-one (1.80 g), cyclopropylboronic acid (2.00 g), Cu(OOCCH$_3$)$_2$ (2.00 g), 2,2'-bipyridine (1.70 g), Na$_2$CO$_3$ (2.47 g), and 1,2-dichloroethane (75 mL) was heated to 70° C. and the mixture was stirred at this temperature in air overnight. Then, another portion of cyclopropylboronic acid (0.50 g) and Na$_2$CO$_3$ (0.55 g) were added and the mixture was further stirred at reflux temperature for another 4 h. After cooling to ambient temperature, aqueous NH$_4$Cl solution was added and the resultant mixture was extracted with dichloromethane. The combined organic extracts were dried (MgSO$_4$) and the solvent was evaporated. The residue was purified by chromatography on silica gel (cyclohexane/ethyl acetate 50:50→35:65) to afford the title compound as an oil that crystallized on standing. Yield: 0.82 g (37% of theory); Mass spectrum (ESI⁺): m/z=214/216 (Br) [M+H]⁺.

EXAMPLE 10

3-{(S)-Cyclopropyl-[4-(1-methyl-6-oxo-1,6-dihydro-pyridin-3-yl)-phenyl]-methyl}-(S)-6-(2-hydroxy-2-methyl-propyl)-6-phenyl-[1,3]oxazinan-2-one

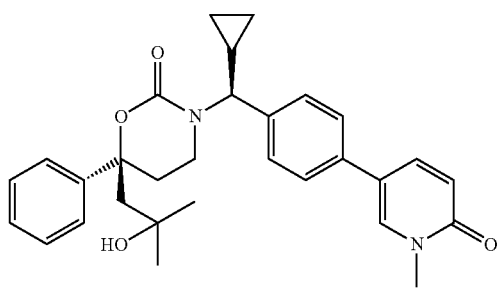

The title compound was prepared from 3-{(S)-cyclopropyl-[4-(4,4,5,5-tetramethyl-[1,3,2]dioxaborolan-2-yl)-phenyl]methyl}-(S)-6-(2-hydroxy-2-methyl-propyl)-6-phenyl-[1,3]oxazinan-2-one {prepared in analogy to the intermediate in Example 3 from 3-[(S)-(4-bromo-phenyl)-cyclopropyl-methyl]-(S)-6-(2-hydroxy-2-methyl-propyl)-6-phenyl-[1,3]oxazinan-2-one} and 5-bromo-1-methyl-1H-pyridin-2-one following a procedure analogous to that described in Example 3. LC-MS (Method 1): $t_R$=3.35 min; Mass spectrum (ESI⁺): m/z=487 [M+H]⁺.

EXAMPLE 11

3-{(S)-Cyclopropyl-[4-(2-methyl-pyrimidin-5-yl)-phenyl]methyl}-(S)-6-(2-hydroxy-2-methyl-propyl)-6-phenyl-[1,3]oxazinan-2-one

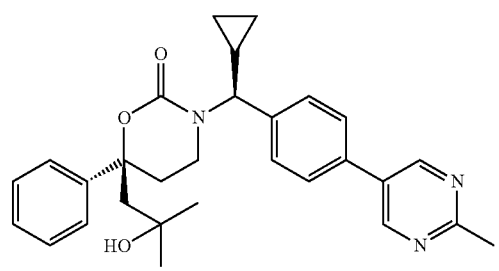

The title compound was prepared from 3-{(S)-cyclopropyl-[4-(4,4,5,5-tetramethyl-[1,3,2]dioxaborolan-2-yl)-phenyl]-methyl}-(S)-6-(2-hydroxy-2-methyl-propyl)-6-phenyl-[1,3]oxazinan-2-one {prepared in analogy to the intermediate in Example 3 from 3-[(S)-(4-bromo-phenyl)-cyclopropyl-methyl]-(S)-6-(2-hydroxy-2-methyl-propyl)-6-phenyl-[1,3] oxazinan-2-one} and 5-bromo-2-methyl-pyrimidine following a procedure analogous to that described in Example 3. LC-MS (Method 1): $t_R$=3.28 min; Mass spectrum (ESI⁺): m/z=472 [M+H]⁺.

BIOLOGICAL TEST EXAMPLE 1

In vitro inhibition of 11 β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 μM) and cortisone (80 nM). Cortisol generated in the reaction was then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals is then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal and $IC_{50}$ curves were generated.

In Table 1 the 11β-HSD 1 inhibitory activities, determined as described above, are compiled.

TABLE 1

| Example | $IC_{50}$ [nM] | Example | $IC_{50}$ [nM] |
|---|---|---|---|
| 1 | 65 | 6 | 53 |
| 2 | 960 | 7 (=3a) | 64 |
| 3 | 111 | 8 | 29 |
| 3b | >4500 | 9 | 38 |
| 4 | >>10000 | 10 | 70 |
| 5 | 35 | 11 | 54 |

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to an 11β-HSD1 inhibitor of the invention, comprise a pharmaceutically acceptable salt of a an 11β-HSD1 inhibitor of the invention and one or more pharmaceutically acceptable carriers therefore. Alternatively, a pharmaceutical composition of the invention may comprise a compound of an 11β-HSD1 inhibitor of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of an 11β-HSD1 inhibitor of the invention, or an enantiomer, diastereomer, or pharmaceutically acceptable salt thereof or composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors, or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

While this invention has been particularly shown and described with references to example embodiments thereof, it will be understood by those skilled in the art that various changes in form and details may be made therein without departing from the scope of the invention encompassed by the appended claims.

What is claimed is:
1. A compound of Formula (I)

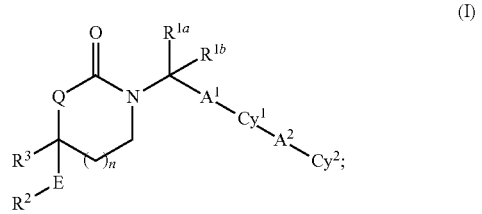

(I)

wherein:
$R^{1a}$ is $(C_3-C_7)$cycloalkyl optionally substituted with up to four groups independently selected from selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$R^{1b}$ is hydrogen, $(C_1-C_6)$alkyl, $(C_2-C_6)$alkenyl, $(C_2-C_6)$alkynyl or $(C_1-C_3)$alkoxy$(C_1-C_3)$alkyl, and the $(C_1-C_6)$alkyl, $(C_2-C_6)$alkenyl, $(C_2-C_6)$alkynyl and $(C_1-C_3)$alkoxy$(C_1-C_3)$alkyl, and the group represented by $R^{1b}$ is optionally substituted with up to four groups independently selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, (b) $(C_1-C_2)$alkylene or $CH_2O$ with the oxygen being attached to $Cy^1$ or $C(=O)$, or (c) $(C_2-C_4)$alkynyl;

$Cy^1$ is aryl, heteroaryl, monocyclic cycloalkyl or monocyclic heterocyclyl and is optionally substituted with 1 to 4 groups independently selected from halogen, —CN, —NO₂, —NH₂, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, —$R^9$, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—NH2, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1-C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$-$C(=O)NR^6R^7$ and —$V^1$—$C(=O)N(R^7)_2$;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl and is optionally substituted with 1 to 4 groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, —R$^9$, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$, and —V$^1$—C(=O)N(R$^7$)$_2$;

E is (a) a bond or (b) (C$_1$-C$_3$)alkylene or (C$_1$-C$_2$)alkylenyloxy, wherein the O is attached to R$^2$, each of which is optionally substituted with 1 to 4 groups independently selected from methyl, ethyl, trifluoromethyl or oxo;

R$^2$ is (C$_1$-C$_6$)alkyl, aryl, heteroaryl, cycloalkyl or heterocyclyl and is optionally substituted with up to 4 groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$- C$_6$)alkenyl, hydroxy(C$_1$-C$_6$)alkoxy, —R$^9$, (C$_1$-C$_6$)alkylthio, (C3-C6)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$;

R$^3$ is selected from (C$_1$-C$_6$)alkyl, (C$_2$-C$_6$)alkenyl, (C$_2$-C$_6$)alkynyl, (C$_3$-$_5$)cycloalkyl(C$_1$-C$_4$)alkyl, (C$_1$-C$_3$)alkoxy (C$_1$-C$_3$)alkoxy, or (C$_1$-C$_3$)alkoxy(C$_1$-C$_3$)alkyl and is optionally substituted with up to four groups independently selected from —H, fluorine, cyano, oxo, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$—C$_6$)alkyl, hydroxy(C$_1$-C$_6$)alkyl, (C$_1$-C$_6$)alkoxy(C$_1$-C$_6$)alkyl, R$^4$O—, (R$^4$)$_2$N—, R$^4$O$_2$C—, R$^4$C(=O)O—, R$^4$S—, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, spirocycloalkyl; heterocyclyl (which in turn is optionally substituted with alkyl, haloalkyl, halogen or oxo), heteroaryl (which in turn is optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido) and heteroarylamino (which in turn is optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo);

n is 0, 1 or 2;

Q is O;

each R$^4$ is independently selected from H, (C$_1$-C$_6$)alkyl, halo(C$_1$-C$_6$)alkyl, amino(C$_1$-C$_6$)alkyl, (C$_1$-C$_6$) alkylamino(C$_1$-C$_6$) alkyl, di(C$_1$-C$_6$)alkylamino (C$_1$-C$_6$) alkyl, hydroxy(C$_1$-C$_6$) alkyl and (C$_1$-C$_6$) alkoxy(C$_1$-C$_6$) alkyl ;

each R$^6$ is independently (C$_1$-C$_6$)alkyl, (C$_2$-C$_6$)alkenyl, (C$_2$-C$_6$)alkynyl or (C$_1$-C$_6$)alkoxy;

V$^1$ is (C$_1$-C$_6$)alkylene, (C$_1$-C$_6$)alkenylene, (C$_1$-C$_6$)alkynylene or (C$_1$-C$_6$)alkyleneoxy;

each R$^7$ is independently (C$_3$-C$_6$)cycloalkyl or (C$_3$-C$_6$) cycloalkoxy;

R$^8$ is heterocyclyl; and

R$^9$ is (C$_4$-C$_7$)cycloalkylalkyl, (C$_4$-C$_7$)cycloalkylalkoxy, (C$_3$-C$_6$)cycloalkyl(C$_2$-C$_4$)alkynyl, halo(C$_1$-C$_6$)alkyl, halo(C$_2$-C$_6$)alkenyl, halo(C$_3$-C$_6$)cycloalkyl, halo(C$_4$-C$_7$)cycloalkylalkyl, halo(C$_1$-C$_6$)alkoxy, halo (C$_3$-C$_6$) cycloalkoxy, halo(C$_4$-C$_7$)cycloalkylalkoxy, (C$_1$-C$_6$) alkoxy(C$_1$-C$_6$)alkoxy, halo(C$_1$-C$_6$)alkoxy(C$_1$-C$_6$) alkoxy, (C$_1$-C$_6$)alkoxy(C$_1$-C$_6$)alkyl or halo(C$_1$-C$_6$) alkoxy(C$_1$-C$_6$)alkyl;

or a pharmaceutically acceptable salt, enantiomer or diastereomer thereof.

2. The compound of claim 1, wherein the compound is represented by structural formula (II):

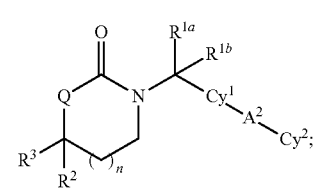

(II)

wherein:

R$^{1a}$ is optionally substituted (C$_3$-C$_5$)cycloalkyl;

R$^{1b}$ is hydrogen or optionally substituted (C$_1$-C$_6$)alkyl; and

Cy$^2$ is an optionally substituted aryl, heteroaryl, cycloalkyl or heterocyclyl group;

or a pharmaceutically acceptable salt, enantiomer or diastereomer thereof.

3. The compound of claim 1, wherein the compound is represented by structural formula (II-A):

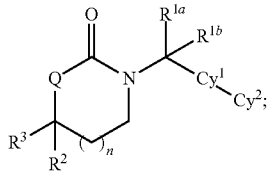

(II-A)

or a pharmaceutically acceptable salt, enantiomer or diastereomer thereof.

4. The compound of claim 1, wherein the compound is represented by structural formula (II-B):

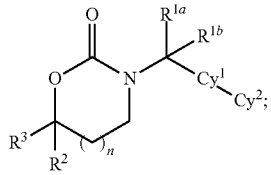

(II-B)

or a pharmaceutically acceptable salt, enantiomer or diastereomer thereof.

5. The compound of claim 1, wherein the compound is represented by structural formula (II-C):

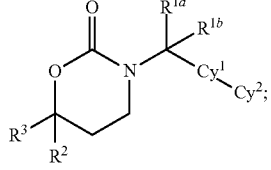

(II-C)

or a pharmaceutically acceptable salt, enantiomer or diastereomer thereof.

6. The compound of claim 1, wherein the compound is represented by structural formula (II-D):

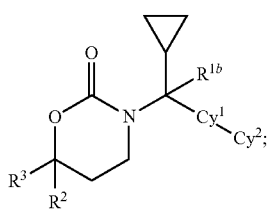

(II-D)

or a pharmaceutically acceptable salt, enantiomer or diastereomer thereof.

7. The compound of claim 1, wherein the compound is represented by structural formula (II-E):

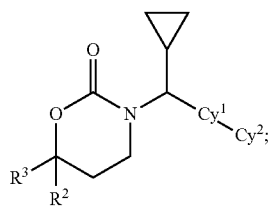

(II-E)

or a pharmaceutically acceptable salt, enantiomer or diastereomer thereof.

8. The compound of claim 1, wherein the compound is represented by structural formula (II-F):

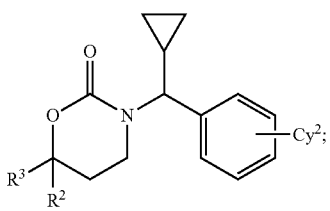

(II-F)

or a pharmaceutically acceptable salt, enantiomer or diastereomer thereof.

9. The compound of claim 1, wherein the compound is represented by structural formula (III):

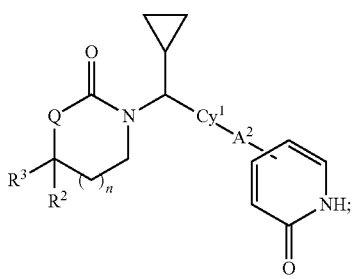

(III)

wherein the oxodihydropyridyl ring in formula (III) is optionally substituted;
or a pharmaceutically acceptable salt, enantiomer or diastereomer thereof.

10. The compound of claim 1, wherein the compound is represented by structural formula (III-A):

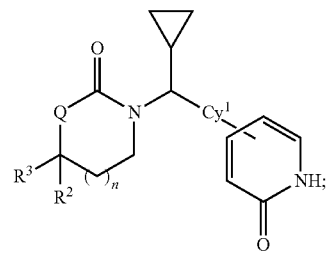

(III-A)

or a pharmaceutically acceptable salt, enantiomer or diastereomer thereof.

11. The compound of claim 1, wherein the compound is represented by structural formula (III-B):

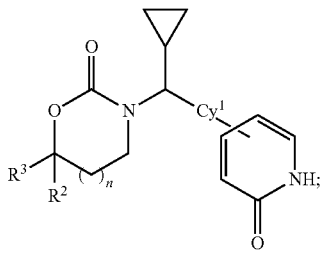

(III-B)

or a pharmaceutically acceptable salt, enantiomer or diastereomer thereof.

12. The compound of claim 1, wherein the compound is represented by structural formula (IV):

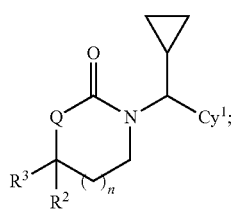

(IV)

or a pharmaceutically acceptable salt, enantiomer or diastereomer thereof.

13. The compound of claim 1, wherein the compound is represented by structural formula (II-H)

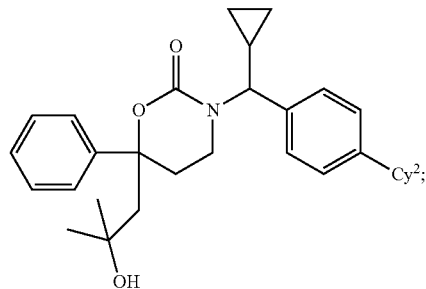

(II-H)

wherein $Cy^2$ is a pyridyl, pyridazinyl or pyrimidinyl group optionally substituted with methyl, cyclopropyl, cyano, $CONH_2$, CONHMe or $CONMe_2$; or a pharmaceutically acceptable salt, enantiomer or diastereomer thereof.

14. The compound of claim 1, wherein the compound is represented by structural formula (II-H)

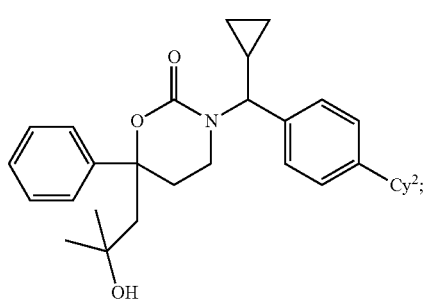

(II-H)

wherein $Cy^2$ is an oxodihydropyridyl group optionally substituted at the ring nitrogen with methyl, ethyl, propyl, isopropyl or cyclopropyl; or a pharmaceutically acceptable salt. enantiomer or diastereomer thereof.

15. A method of treating a subject with a disease associated with the activity or expression of 11β-HSD1, comprising the step of administering to the subject an effective amount of the compound of claim 1.

16. A pharmaceutical composition comprising: i) a pharmaceutically acceptable carrier or diluent; and ii) the compound of claim 1; or a pharmaceutically acceptable salt, enantiomer or diastereomer thereof.

* * * * *

UNITED STATES PATENT AND TRADEMARK OFFICE
CERTIFICATE OF CORRECTION

PATENT NO. : 8,703,765 B2
APPLICATION NO. : 13/375238
DATED : April 22, 2014
INVENTOR(S) : Frank Himmelsbach It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 191 days.

Signed and Sealed this

Twenty-ninth Day of September, 2015

Michelle K. Lee
*Director of the United States Patent and Trademark Office*